(12) United States Patent
Schmitt et al.

(10) Patent No.: US 11,923,067 B2
(45) Date of Patent: Mar. 5, 2024

(54) METHOD AND APPARATUS FOR AUTOMATED DETERMINATION OF STENT LANDING ZONES BASED ON A MAXIMUM DIAMETER OF A SEGMENTED BLOOD VESSEL DATA OBTAINED BY INTRAVASCULAR DEVICE

(71) Applicant: Lightlab Imaging, Inc., Westford, MA (US)

(72) Inventors: Joseph M. Schmitt, Andover, MA (US); Hiram Bezerra, Shaker Heights, OH (US); Christopher Petroff, Groton, MA (US); Ajay Gopinath, Waltham, MA (US)

(73) Assignee: LightLab Imaging, Inc., Westford, MA (US)

( * ) Notice: Subject to any disclaimer, the term of this patent is extended or adjusted under 35 U.S.C. 154(b) by 457 days.

(21) Appl. No.: 14/115,527

(22) PCT Filed: Mar. 12, 2013

(86) PCT No.: PCT/US2013/030328
§ 371 (c)(1),
(2) Date: Nov. 4, 2013

(87) PCT Pub. No.: WO2014/092755
PCT Pub. Date: Jun. 19, 2014

(65) Prior Publication Data
US 2015/0297373 A1    Oct. 22, 2015

Related U.S. Application Data

(60) Provisional application No. 61/736,226, filed on Dec. 12, 2012.

(51) Int. Cl.
*G16H 30/20* (2018.01)
*A61B 5/00* (2006.01)
(Continued)

(52) U.S. Cl.
CPC .......... *G16H 30/20* (2018.01); *A61B 5/0066* (2013.01); *A61B 5/02007* (2013.01);
(Continued)

(58) Field of Classification Search
CPC ................ A61B 5/1076–1079; A61B 5/02007
See application file for complete search history.

(56) References Cited

U.S. PATENT DOCUMENTS

| | | | |
|---|---|---|---|
| 5,054,492 A | 10/1991 | Scribner et al. | |
| 5,321,501 A | 6/1994 | Swanson et al. | |

(Continued)

FOREIGN PATENT DOCUMENTS

| | | | |
|---|---|---|---|
| CN | 1695568 A | 11/2005 | |
| CN | 1871998 A | 12/2006 | |

(Continued)

OTHER PUBLICATIONS

Wong et al _2008_Determination of fractional flow reserve (FFR) based on scaling laws.*

(Continued)

*Primary Examiner* — Serkan Akar
(74) *Attorney, Agent, or Firm* — Lerner David LLP

(57) ABSTRACT

In part, the invention relates to a method for sizing a stent for placement in a vessel. In one embodiment, the method includes the steps of: dividing the vessel into a plurality of segments, each segment being defined as the space between branches of the vessel; selecting a starting point that appears to have substantially no disease; defining the diameter at this point to be the maximum diameter; calculating the maximal diameter of the next adjacent segment according to a power law; measuring the actual diameter of the next adjacent segment; selecting either the calculated maximum diameter or the measured maximum diameter depending upon which diameter is larger; using the selected maximum diameter to (Continued)

find the maximum diameter of this next segment; iteratively proceeding until the entire length of the vessel is examined; and selecting a stent in response to the diameters of the end proximal and distal segments.

21 Claims, 16 Drawing Sheets

(51) Int. Cl.
*A61B 5/02* (2006.01)
*A61B 5/107* (2006.01)
*A61B 90/00* (2016.01)
*A61F 2/82* (2013.01)
*A61F 2/86* (2013.01)
*G16H 20/40* (2018.01)

(52) U.S. Cl.
CPC .............. *A61B 5/1076* (2013.01); *A61F 2/86* (2013.01); *G16H 20/40* (2018.01); *A61B 2090/061* (2016.02); *A61F 2/82* (2013.01); *A61F 2230/0069* (2013.01); *A61F 2240/001* (2013.01); *A61F 2250/006* (2013.01)

(56) References Cited

U.S. PATENT DOCUMENTS

| | | | |
|---|---|---|---|
| 5,459,570 A | 10/1995 | Swanson et al. | |
| 5,465,147 A | 11/1995 | Swanson | |
| 5,477,858 A | 12/1995 | Norris et al. | |
| 5,488,674 A | 1/1996 | Burt et al. | |
| 5,509,093 A | 4/1996 | Miller et al. | |
| 5,531,227 A | 7/1996 | Schneider | |
| 5,619,368 A | 4/1997 | Swanson | |
| 5,662,109 A | 9/1997 | Hutson | |
| 5,748,598 A | 5/1998 | Swanson et al. | |
| 5,771,895 A | 6/1998 | Slager | |
| 5,784,352 A | 7/1998 | Swanson et al. | |
| 5,797,849 A | 8/1998 | Vesely et al. | |
| 5,956,355 A | 9/1999 | Swanson et al. | |
| 5,989,189 A | 11/1999 | LeBlanc et al. | |
| 6,111,645 A | 8/2000 | Tearney et al. | |
| 6,134,003 A | 10/2000 | Tearney et al. | |
| 6,148,095 A | 11/2000 | Prause et al. | |
| 6,160,826 A | 12/2000 | Swanson et al. | |
| 6,191,862 B1 | 2/2001 | Swanson et al. | |
| 6,208,883 B1 | 3/2001 | Holupka et al. | |
| 6,282,011 B1 | 8/2001 | Tearney et al. | |
| 6,381,350 B1 | 4/2002 | Klingensmith et al. | |
| 6,385,332 B1 | 5/2002 | Zahalka et al. | |
| 6,421,164 B2 | 7/2002 | Tearney et al. | |
| 6,445,939 B1 | 9/2002 | Swanson et al. | |
| 6,471,656 B1 | 10/2002 | Shalman et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,585,660 B2 | 7/2003 | Dorando et al. | |
| 6,697,667 B1 | 2/2004 | Lee et al. | |
| 6,706,004 B2 | 3/2004 | Tearney et al. | |
| 6,716,178 B1 | 4/2004 | Kilpatrick et al. | |
| 6,785,409 B1 | 8/2004 | Suri | |
| 6,868,736 B2 | 3/2005 | Sawatari et al. | |
| 6,879,851 B2 | 4/2005 | McNamara et al. | |
| 6,891,984 B2 | 5/2005 | Petersen et al. | |
| 6,947,040 B2 | 9/2005 | Tek et al. | |
| 7,134,994 B2 | 11/2006 | Alpert et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,329,223 B1 | 2/2008 | Ainsworth et al. | |
| 7,359,554 B2 | 4/2008 | Klingensmith et al. | |
| 7,414,779 B2 | 8/2008 | Huber et al. | |
| 7,415,049 B2 | 8/2008 | Flanders et al. | |
| 7,450,241 B2 | 11/2008 | Zuluaga | |
| 7,532,920 B1 | 5/2009 | Ainsworth et al. | |
| 7,593,559 B2 | 9/2009 | Toth et al. | |
| 7,610,081 B2 | 10/2009 | Redel | |
| 7,619,646 B2 | 11/2009 | Freifeld et al. | |
| 7,625,366 B2 | 12/2009 | Atlas | |
| 7,627,156 B2 | 12/2009 | Margolis et al. | |
| 7,650,179 B2 | 1/2010 | Redel et al. | |
| 7,679,754 B2 | 3/2010 | Zuluaga | |
| 7,693,563 B2 | 4/2010 | Suresh et al. | |
| 7,706,585 B2 | 4/2010 | Kleen | |
| 7,729,746 B2 | 6/2010 | Redel et al. | |
| 7,733,497 B2 | 6/2010 | Yun et al. | |
| 7,783,338 B2 | 8/2010 | Ainsworth et al. | |
| 7,785,286 B2 | 8/2010 | Magnin et al. | |
| 7,801,343 B2 | 9/2010 | Unal et al. | |
| 7,813,609 B2 | 10/2010 | Petersen et al. | |
| 7,831,078 B2 | 11/2010 | Unal et al. | |
| 7,843,976 B2 | 11/2010 | Cable et al. | |
| 7,848,791 B2 | 12/2010 | Schmitt et al. | |
| 7,872,759 B2 | 1/2011 | Tearney et al. | |
| 7,916,387 B2 | 3/2011 | Schmitt | |
| 7,930,014 B2 | 4/2011 | Huennekens et al. | |
| 7,935,060 B2 | 5/2011 | Schmitt et al. | |
| 8,029,447 B2 | 10/2011 | Kanz et al. | |
| 8,116,605 B2 | 2/2012 | Petersen et al. | |
| 8,206,377 B2 | 6/2012 | Petroff | |
| 8,208,995 B2 | 6/2012 | Tearney et al. | |
| 8,223,143 B2 | 7/2012 | Dastmalchi et al. | |
| 8,298,147 B2 | 10/2012 | Huennekens et al. | |
| 8,315,282 B2 | 11/2012 | Huber et al. | |
| 8,325,419 B2 | 12/2012 | Schmitt | |
| 8,358,461 B2 | 1/2013 | Huber et al. | |
| 8,412,312 B2 | 4/2013 | Judell et al. | |
| 8,449,468 B2 | 5/2013 | Petersen et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,687,201 B2 | 4/2014 | Adler | |
| 8,786,336 B1 | 7/2014 | Schmitt | |
| 8,831,321 B1 | 9/2014 | Elbasiony | |
| 8,948,228 B2 | 2/2015 | Adler | |
| 8,953,911 B1 | 2/2015 | Xu et al. | |
| 8,983,580 B2 | 3/2015 | Boppart et al. | |
| 2002/0115931 A1 | 8/2002 | Strauss et al. | |
| 2002/0161351 A1 | 10/2002 | Samson et al. | |
| 2003/0200120 A1* | 10/2003 | Binkert | G16H 50/50 702/19 |
| 2005/0201662 A1 | 9/2005 | Petersen et al. | |
| 2005/0238067 A1 | 10/2005 | Choi | |
| 2005/0249391 A1 | 11/2005 | Kimmel et al. | |
| 2006/0095065 A1 | 5/2006 | Tanimura et al. | |
| 2006/0135870 A1 | 6/2006 | Webler | |
| 2006/0165270 A1 | 7/2006 | Borgert et al. | |
| 2006/0203859 A1 | 9/2006 | Cable et al. | |
| 2006/0241469 A1 | 10/2006 | Rold et al. | |
| 2007/0060822 A1 | 3/2007 | Alpert et al. | |
| 2007/0092067 A1 | 4/2007 | Fujisawa | |
| 2007/0165916 A1 | 7/2007 | Cloutier et al. | |
| 2007/0232933 A1 | 10/2007 | Gille et al. | |
| 2007/0293932 A1 | 12/2007 | Zilla et al. | |
| 2008/0228086 A1* | 9/2008 | Ilegbusi | A61B 5/0066 600/479 |
| 2008/0281205 A1 | 11/2008 | Naghavi et al. | |
| 2009/0027051 A1 | 1/2009 | Stuber et al. | |
| 2009/0174931 A1 | 7/2009 | Huber et al. | |
| 2009/0204134 A1 | 8/2009 | Kassab | |
| 2009/0306520 A1 | 12/2009 | Schmitt et al. | |
| 2010/0076320 A1 | 3/2010 | Petersen et al. | |
| 2010/0094127 A1 | 4/2010 | Xu | |
| 2010/0234678 A1 | 9/2010 | Pryor et al. | |
| 2010/0253949 A1 | 10/2010 | Adler et al. | |
| 2011/0034801 A1 | 2/2011 | Baumgart | |
| 2011/0071404 A1 | 3/2011 | Schmitt et al. | |

(56) References Cited

U.S. PATENT DOCUMENTS

| | | | |
|---|---|---|---|
| 2011/0071405 | A1 | 3/2011 | Judell et al. |
| 2011/0101207 | A1 | 5/2011 | Schmitt |
| 2011/0157686 | A1 | 6/2011 | Huber et al. |
| 2011/0190586 | A1 | 8/2011 | Kemp |
| 2011/0228280 | A1 | 9/2011 | Schmitt et al. |
| 2011/0257545 | A1 | 10/2011 | Suri |
| 2011/0282586 | A1 | 11/2011 | Kassab et al. |
| 2012/0075638 | A1 | 3/2012 | Rollins et al. |
| 2012/0310081 | A1 | 6/2012 | Adler et al. |
| 2012/0238869 | A1 | 9/2012 | Schmitt et al. |
| 2012/0250028 | A1 | 10/2012 | Schmitt et al. |
| 2012/0253184 | A1 | 10/2012 | Furuichi et al. |
| 2013/0010303 | A1 | 1/2013 | Petersen et al. |
| 2013/0012800 | A1 | 1/2013 | Schmitt et al. |
| 2013/0023761 | A1 | 1/2013 | Petroff |
| 2013/0051728 | A1 | 2/2013 | Petroff |
| 2013/0072805 | A1 | 3/2013 | Schmitt et al. |
| 2013/0310698 | A1 | 11/2013 | Judell et al. |
| 2014/0018669 | A1 | 1/2014 | Xu |
| 2014/0024931 | A1 | 1/2014 | Winston et al. |
| 2014/0094697 | A1 | 4/2014 | Petroff et al. |
| 2014/0114182 | A1 | 4/2014 | Petersen et al. |
| 2014/0142427 | A1 | 5/2014 | Petroff |
| 2014/0142432 | A1 | 5/2014 | Hutchins et al. |
| 2014/0142436 | A1 | 5/2014 | Hutchins et al. |
| 2014/0187929 | A1 | 7/2014 | Schmitt et al. |
| 2014/0218742 | A1 | 8/2014 | Adler |
| 2014/0249407 | A1 | 9/2014 | Adler et al. |
| 2014/0268167 | A1 | 9/2014 | Friedman et al. |
| 2014/0276011 | A1 | 9/2014 | Schmitt et al. |
| 2014/0309536 | A1 | 10/2014 | Douk et al. |
| 2014/0379269 | A1 | 12/2014 | Schmitt |

FOREIGN PATENT DOCUMENTS

| | | |
|---|---|---|
| CN | 1973772 A | 6/2007 |
| CN | 101493940 | 7/2009 |
| CN | 102781508 | 11/2012 |
| EP | 2062526 | 5/2009 |
| EP | 2505118 A1 | 10/2012 |
| EP | 2744400 | 5/2017 |
| JP | 2010523268 A | 7/2010 |
| JP | 2012157384 A | 8/2012 |
| JP | 2012200532 A | 10/2012 |
| WO | 2006076409 | 7/2006 |
| WO | 2007002685 | 1/2007 |
| WO | 20110038044 | 3/2011 |
| WO | 2012034098 A3 | 6/2012 |

OTHER PUBLICATIONS

Patent Examination Report issued by IP Australia dated Mar. 30, 2016, for Patent Application No. 2013360356 (7 pages).

Jain et al., "Unsupervised Texture Segmentation Using Gabor Filters", Pattern Recognition, vol. 24, 1167-1186 (1991).

Randen et al., "Filtering for Texture Classification: A Comparitive Study", IEEE Trans on Pattern Analysis and Machine Intelligence, vol. 21, 291-310 (1999).

Briguori et al., "Intravascular ultrasound guidance for the functional assessment of intermediate coronary artery stenoses and comparison with fractional flow reserve," Am J. Cardiol 87:136-141, 2001.

Kassab et al., "The pattern of coronary arteriolar bifurcations and the uniform shear hypothesis," Annals of Biomedical Engineering 23 (1): 13-20, 1995.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.

Kolyva et al., "Increased diastolic time fraction as beneficial adjunct of α1-adrenergic receptor blockade after percutaneous coronary intervention," Am J Physiol Heart Circ Physiol 295: H2054-H2060, 2008.

Kolyva et al., "'Windkesselness' of coronary arteries hampers assessment of human coronary wave speed by single-point technique," Am J Physiol Heart Circ Physiol, 295: H482-H490, 2008.

Laslett, "Normal left main coronary artery diameter can be predicted from diameters of its branch vessels," Clinical Cardiology 18 (10): 580-582, 1995.

Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.

Ohta et al., "Rheological Changes After Stenting of a Cerebral Aneurysm: A Finite Element Modeling Approach," Cardiovascular and Interventional Radiology (2005) 28:768-772.

Pijls et al., "Fractional Flow Reserve (FFR) Post-Stent Registry Investigators Coronary pressure measurement after stenting predicts adverse events at follow-up: a multicenter registry", Circulation 2002; 105:2950 -2954.

Seiler et al., "Basic structure-function relations of the epicardial coronary vascular tree, Basis of quantitative coronary arteriography for diffuse coronary artery disease," Circulation 85 (6): 1987-2003, 1992.

Siebes et al., "Single-wire pressure and flow velocity measurement to quantify coronary stenosis hemodynamics and effects of percutaneous interventions," Circulation 109:756-762, 2004.

Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).

Spaan, "Coronary Blood Flow," Ch 12. Dordrecht, The Netherlands: Kluwer Acedemic Publishers, Boston; 1991: pp. 333-361.

Takagi et al., "Clinical potential of intravascular ultrasound for physiological assessment of coronary stenosis," Circulation 100: 250-255, 1999.

Verhoeff et al., "Influence of percutaneous coronary intervention on coronary microvascular resistance index," Circulation 111:76-82, 2005.

White et al., "Does visual interpretation of the coronary angiogram predict the physiologic importance of coronary stenoses?," N. Engl J Med 310:13 819-824, 1984.

Wilson et al., "Prediction of the physiologic significance of coronary arterial lesions by quantitative lesion geometry in patients with limited coronary artery disease," Circulation 75: 723-732, 1987.

PCT International Search Report and Written Opinion of International Searching Authority for International Patent Application No. PCT/US2010/049887, dated Jun. 9, 2011, 19 pages.

Herrington et al., "Semi-automated boundary detection for intravascular ultrasound," Computers in Cardiology 1992 Proceedings., pp. 103-106, Oct. 1992.

Sonka et al., "Segmentation of intravascular ultrasound images: a knowledge-based approach," IEEE Transactions on Medical Imaging, 14(4):719-732, Dec. 1995.

Mojsilovic et al., "Automatic segmentation of intravascular ultrasound images: A texture-based approach," Annals of Biomedical Engineering, 25:1059-1071, Nov. 1997.

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Kovalski et al., "Three-dimensional automatic quantitative analysis of intravascular ultrasound images," Ultrasound in Medicine & Biology, 26(4):527-537, 2000.

(56) References Cited

OTHER PUBLICATIONS

Pujol et al., "Intravascular Ultrasound Images Vessel Characterization using AdaBoost," Functional Imaging and Modeling of the Heart: Lecture Notes in Computer Science, pp. 242-251, 2003.
Taki et al., "Automatic segmentation of calcified plaques and vessel borders in IVUS images," International Journal of Computer Assisted Radiology and Surgery, 3(3-4):347-354, Sep. 2008.
Van den Berg et al., "Using three-dimensional rotational angiography for sizing of covered stents," Am. J. Roentgenology, 178:149-152 (2002).
Wong et al., "A novel method of coronary stent sizing using intravascular ultrasound: safety and clinical outcomes," Int. J. Angiol. , 18(1): 22-24 2009.
International Preliminary Report on Patentability and Written Opinion of the International Searching Authority dated Jun. 16, 2015 for International application No. PCT/2013/030328 (13 pages).
International Search Report for International Application No. PCT/US2009/060714, dated Jan. 4, 2010 (6 pages).
Written Opinion of the International Searching Authority for International Application No. PCT/US2009/060714, dated Jan. 4, 2010 (10 pages).
Mittal et al., Analysis of blood flow in the entire coronary arterial tree, Am J Physiol Heart Circ Physiol 289: H439-H446 (2005).
Bonnema et al., "An automatic algorithm for detecting stent endothelialization from volumetric optical coherence tomography datasets", Physics in Medicine and Biology, 53:12, Jun. 21, 2008, pp. 3083-3098.
Unal et al., "Stent implant follow-up in intravascular optical coherence tomography images", Int J Cardiovasc Imaging, DOI 10.1007/s10554-009-9508-4, published online Sep. 24, 2009 (8 pages).
Xu et al., "Characterization of atherosclerosis plaques by measuring both backscattering and attenuation coefficients in optical coherence tomography", Journal of Biomedical Optics, 13:3, May/Jun. 2008 (8 pages).
Takano et al., "Evaluation by Optical Coherence Tomography of Neointimal Coverage of Sirolimus-Eiutine Stent Three Months After Implantation," American Journal of Cardiology, 99:8, Apr. 14, 2007, pp. 1033-1038.
International Search Report and Written Opinion of the International Searching Authority for International Application No. PCT/US2013/029855 dated Jun. 17, 2013 (10 pages).
Oshima, "Intravascular Ultrasound Analysis of the Radial Artery for Coronary Artery Bypass Grafting", Ann Thorac Surg 2005; 79:99-103.
Guagliumia et al., "The Race to Achieve the Gold Standard in Coronary Imaging", Rev Esp Cardiol. 2009;62(6):599-602.
Hahn, "Serial Intravascular Ultrasound Analysis of the Main and Side Branches in Bifurcation Lesions Treated with the T-Stenting Technique", JACC 54:2, Jul. 7, 2009, pp. 110-117.
Olson et al., "Chord length distributions in binary stochastic media in two and three dimensions", Journal of Quantitative Spectroscopy & Radiative Transfer 101 (2006) 269-283.
Pazos et al., "Mechanical Characterization of Atherosclerotic Arteries Using Finite-Element Modeling: Feasability Study on Mock Arteries", IEEE Transactions on Biomedical Engineering, 57:6, Jun. 2010.
Sanz et al., "Development of Software for Three-Dimensional Reconstruction and Automatic Quantification of Intravascular Ultrasound (IVUS)," Initial Experience, Rev Esp Cardiol. 2006;59(9):879-88.
Virmani et al., "Localized Hypersensitivity and Late Coronary Thrombosis Secondary to a Sirolimus-Eluting Stent Should We Be Cautious?", Circulation, Feb. 17, 2004.
Zhou et al., On the design of the coronary arterial tree: a generalization of Murray's law, Phys. Med. Biol. 44 (1999) 2929-2945.
Wang et al., "Image Quality Assessment: From Error Visibility to Structural Similarity", IEEE Transactions on Image Processing, 13:4, pp. 1-14 (Apr. 2004).
Kume et al., "Assessment of Coronary Intima—Media Thickness by Optical Coherence Tomography—Comparison With Intravascular Ultrasound", Circ J 2005; 69: 903-907.
Sera et al., "Optimal Stent-Sizing with Intravascular Ultrasound Contributes to Complete Neointimal Coverage After Sirolimus-Eluting Stent Implantation Assessed by Angioscopy", JACC: Cardiovascular Interventions, vol. 2, No. 10 2009, Oct. 2009:989-94.
Taylor et al., "Patient-specific Modeling of Cardiovascular Mechanics", Annu Rev Biomed Eng. Author manuscript; available in PMC Sep. 24, 2015, pp. 1-31.
Xiong, "Computational Methods of Modeling Vascular Geometry and Tracking Pulmonary Motion Form Medical Images", Dissertation online at http://purl.stanfor.edu/rv373cz9473, 134 pages.
Ali et al., "Optical coherence tomography compared with intravascular ultrasound and with angiography to guide coronary stent implantation (Ilumien III: Optimize PCI): a randomised controlled trial", www.thelancet.com, Published online Oct. 30, 2016, http://dx.doi.org/10.1016/S0140-6736(16)31922-5, 11 pages.
Chinese Search Report for Application No. 1810361340.5 dated Sep. 22, 2020, 1 page.
Japanese Notice of Allowance for Application No. 2018088554 dated Aug. 11, 2020, 3 pages.

* cited by examiner a'

(PRIOR ART)

METHOD AND APPARATUS FOR AUTOMATED DETERMINATION OF STENT LANDING ZONES BASED ON A MAXIMUM DIAMETER OF A SEGMENTED BLOOD VESSEL DATA OBTAINED BY INTRAVASCULAR DEVICE

RELATED APPLICATION

This application is a national phase under 35 U.S.C. § 371 of International Application No. PCT/US2013/030328, filed on Mar. 12, 2013, which claims priority to and the benefit of provisional patent application, Ser. No. 61/736,226, filed on Dec. 12, 2012, the entire disclosures of each of which are incorporated herein by reference.

BACKGROUND

Most interventional cardiologists during stenting procedures rely on angiography to correctly size and position the stent. Unfortunately, when using angiographic projections, the eccentricity of lumen cross sections makes accurate measurement of vessel diameters difficult for stent sizing. Further, differentiation of normal and diseased segments in diffuse lesions is also difficult because angiography is not able to directly visualize plaque in the vessel wall. These limitations of angiography make proper stent sizing and positioning a challenge. Improper stent sizing can cause significant damage to the vessel if the stent is oversized or inadequate therapeutic value if the stent is undersized.

Although optical coherence tomography (OCT) and intravascular ultrasound (IVUS) do not suffer from the limitations inherent in angiography, OCT and IVUS imaging modalities guide stent deployment in only a small fraction of interventional procedures. One reason for the limited use of OCT and IVUS imaging for stent deployment is that the current procedures for determining the optimal diameter and length of the stent are subjective and time-consuming. There is a need for a simple and fast method for applying intravascular imaging information to properly size and deploy stents to yield the best possible restoration of the normal vessel contours.

The present invention addresses this need and others.

SUMMARY OF THE INVENTION

In one aspect, the invention relates to a method for sizing and adjusting a stent for restoration of the contour of a narrowed vessel. In one embodiment, the method includes the steps of: dividing the vessel into a plurality of segments, each segment being defined as the space between branches of the vessel; selecting a starting point that appears to have substantially no plaque; defining the diameter at this point to be the maximum diameter; calculating the maximal diameter of the next adjacent segment according to a power law; measuring the actual diameter of the next adjacent segment; selecting either the calculated maximum diameter or the measured maximum diameter depending upon which diameter is larger; using the selected maximum diameter to find the maximum diameter of this next segment; iteratively proceeding until every segment of the vessel in which the stent is to be placed is examined; and selecting a stent in response to the diameters of the end proximal and distal segments.

In one embodiment, the maximum diameter of a segment is determined in response to its measured diameter, its calculated mean diameter and its quality. In another embodiment, the power law is given by the expression:

$$D^\varepsilon(i+1) = D^\varepsilon(i) + D_b^\varepsilon(i)$$

where D is the diameter of the segment, $D_b$ is the diameter of the branch, and ε is the exponent. In still yet another embodiment, ε has a value between about 2.0 and about 3.0. In another embodiment, the normality of the tissue is determined by a method selected from the group of automated tissue characterization, user identification and morphology. In another embodiment, the method of automated tissue characterization utilizes cross-correlation of the OCT signal between adjacent regions of the vessel. In yet another embodiment, the method of automated tissue characterization utilizes IM to OA ratios. In yet another embodiment, frames of interest are first filtered with a Gabor filter. In still yet another embodiment, the method of automated tissue characterization utilizes frame based intensity profiles. In another embodiment, the method further comprises determining where in the vessel the stent should make contact by determining the amount of disease present in the vessel.

In another aspect, the invention relates to an apparatus for sizing a stent for placement in a vessel. In one embodiment, the apparatus includes a processor having imaging data for the vessel, the processor executing program having the steps: dividing the vessel into a plurality of segments, each segment being defined as the space between branches of the vessel; selecting a starting point that appears to have substantially no plaque; defining the diameter at this point to be the maximum diameter; calculating the maximal diameter of the next adjacent segment according to a power law; measuring the actual diameter of the next adjacent segment; selecting either the calculated maximum diameter or the measured maximum diameter depending upon which diameter is larger; using the selected maximum diameter to find the maximum diameter of this next segment; and iteratively proceeding until every segment of the vessel in which the stent is to be placed is examined; and displaying the results to allow a user to select a stent in response to the diameters of the end proximal and distal segments.

In one embodiment, the processor determines the maximum diameter of a segment in response to the measured diameter of the segment, the calculated diameter of the segment, and the quality of the segment. In another embodiment, the processor calculates the calculated diameter of a segment from a power law is given by the expression:

$$D^\varepsilon(i+1) = D^\varepsilon(i) + D_b^\varepsilon(i)$$

where D is the diameter of the segment, $D_b$ is the diameter of the branch and ε is the exponent. In yet another embodiment, ε has a value between about 2.0 and about 3.0. In still yet another embodiment, the apparatus determines the normalcy of the tissue by a method selected from the group of automated tissue characterization, user identification and morphology. In one embodiment, automated tissue characterization utilizes cross-correlation of the OCT signal between adjacent regions of the vessel. In another embodiment, automated tissue characterization utilizes IM to OA ratios. In yet another embodiment, the processor first filters image data of the vessel segments using a Gabor filter. In still yet another embodiment, the processor performs automated tissue characterization utilizing frame-based intensity profiles. In another embodiment, the processor determines where in the vessel the stent should make contact by determining the amount of disease present in the vessel.

In another aspect, the invention relates to a processor-based method of displaying a representation of a section of a blood vessel. In one embodiment, the method includes generating a set of data in response to distance measurements of the section of the blood vessel using an optical coherence tomography system, the set comprising a plurality of cross-sectional areas at a plurality of positions along the section; displaying a first panel having a first axis and a second axis, the first panel comprising a first longitudinal image view of the section of the blood vessel, wherein the first axis corresponds to a diameter value, wherein the second axis corresponds to a position along the section of the blood vessel; and displaying a minimum lumen area for the section of the blood vessel. In another embodiment, the diameter value is displayed as a mean diameter or a measured diameter. In yet another embodiment, the step of generating the first longitudinal view uses a plurality of mean cross-sectional diameters.

In another embodiment, the method includes displaying, in a second panel, a longitudinal view of the of the section of the blood vessel, wherein the first axis corresponds to a diameter value, wherein the second axis corresponds to a position along the section of the blood vessel and a branch of the blood vessel as a perpendicular bar. In yet another embodiment, the width of the bar is sized such that it equals the width of the branch.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIG. 9b is an image of the A-line patch of FIG. 9a;

DETAILED DESCRIPTION

Optical coherence tomography (OCT), intravascular ultrasound (IVUS) and other intravascular imaging modalities provide valuable information about vessel dimensions and plaque characteristics. However, current imaging systems do not present this information in a way that is easy to interpret for proper stent selection and deployment.

Figure 1:
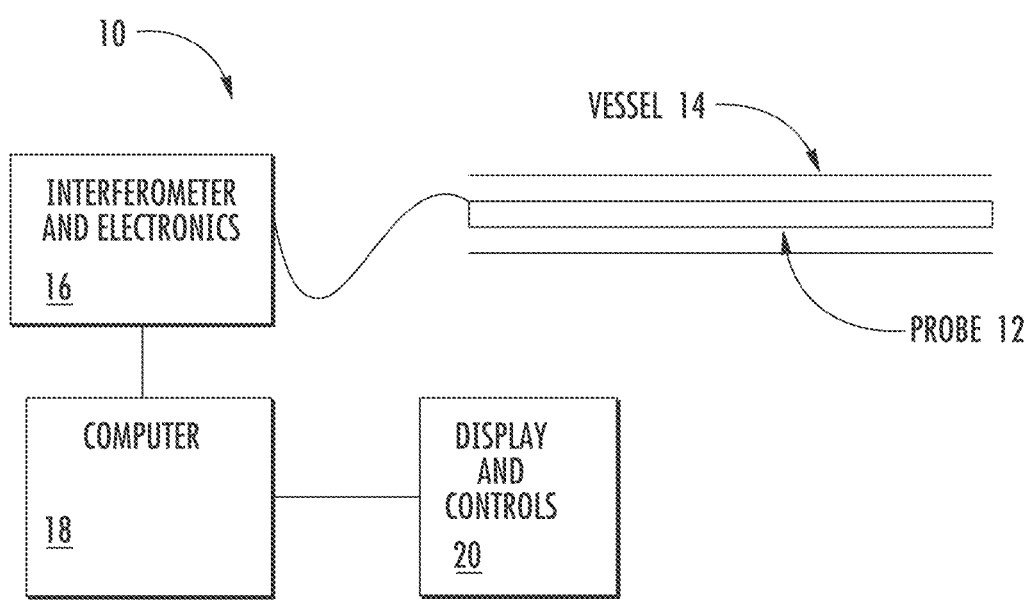
FIG. 1 is a block diagram of an embodiment of a system constructed in accordance with the invention.

FIG. 1 is a block diagram of an embodiment of an OCT system 10 constructed in accordance to the present invention. The system 10 includes an optical probe 12 sized for insertion into the blood vessel of interest 14. Light is passed into the probe 12 and light reflections from the tissue received from the probe 12 and passed to an interferometric and electronics module 16. The electronic signals corresponding to light received from the probe 12 are passed to a processor module 18 and manipulated as described herein. The results are displayed on a graphics display and control unit 20.

Figures 2A, 2B:
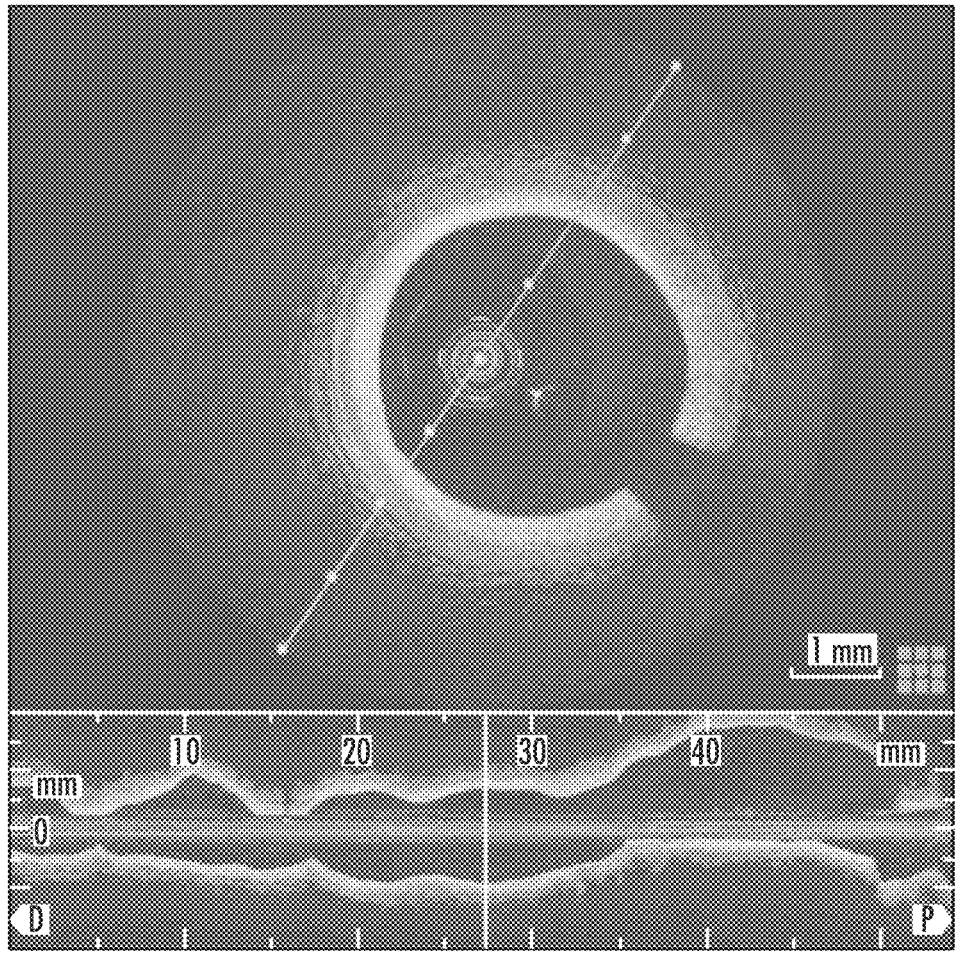
FIGS. 2 a and b are an embodiment of an OCT display screen showing both a cross sectional display of an vessel (FIG. 2a) and a longitudinal cross section of the vessel (FIG. 2b)

FIGS. 2a and 2b show an embodiment of a commercially available OCT system display that depicts images obtained from a coronary artery. A single transverse cross-sectional image of a blood vessel is displayed at a user-selected longitudinal position (FIG. 2a), along with a single longitudinal cross section (shown as a vertical line (a-a') through the longitudinal image of FIG. 2b) at a user-selected angle and location within the vessel. As the user chooses various locations in the longitudinal image of FIG. 2b, the cross section at that location appears in FIG. 2a.

Using the recorded images as a guide, a cardiologist typically employs a multi-step process to extract the information needed to choose the appropriate size and length of a stent for treating a lesion such as a stenosis caused by plaque. The steps generally required are: looking through the image set to find narrowest lumen cross section; measuring the minimum lumen area (MLA); looking through the image set in a distal direction starting from the frame with the current MLA to locate the vessel cross section with the lowest plaque burden and largest lumen diameter. Next, the cardiologist measures and records the mean diameter of this cross section as the distal reference diameter, $D_d$ and repeats the search for the vessel cross section with the lowest plaque burden and largest lumen diameter, except that the cardiologist scrolls through the image set in the proximal direction instead of the distal direction. When this cross section is found, the cardiologist measures and records the mean diameter of this cross section as the proximal reference diameter, $D_p$. Next, the cardiologist rotates the longitudinal cut plane to locate any large branches and plaque characteristics that may influence the placement of the stent and its expanded diameter.

If necessary, the cardiologist then readjusts the positions of the reference cross sections to account for the presence of nearby branches. Once this is complete, the cardiologist then must measure the distance L in mm between the proximal and distal reference cross sections and choose a stent with a length greater than the segment length L and with a diameter between $D_d$ and $D_p$ that will, after expansion, ensure good strut apposition without overextending the arterial wall. If necessary, the cardiologist then must plan for post-dilation with a balloon catheter to taper the stent diameter to achieve better conformance with the normal taper of the vessel lumen.

In a busy catheterization laboratory, these steps can be excessively time-consuming and difficult to carry out reliably. Added complications can arise if the lesion is diffuse and plaque is present throughout the imaged segment or if one or more large side branches are present, which makes reference frames difficult to identify and the degree of vessel tapering difficult to evaluate.

Not only are OCT and IVUS important methodologies for pre-interventional stent planning, OCT and IVUS imaging are also valuable for assessing the quality of stent expansion after implantation. As in the stent deployment procedure, vessel cross sections located proximal and distal to the implanted stent are used as references to judge whether the stent has been expanded properly. In current practice, these reference cross sections are usually found by using a subjective manual procedure similar to the one outlined above. As a result, similar difficulties with lumen tapering and side branches are often encountered, which hinder quantification of target diameters for balloon dilation as presently used.

Figure 3:
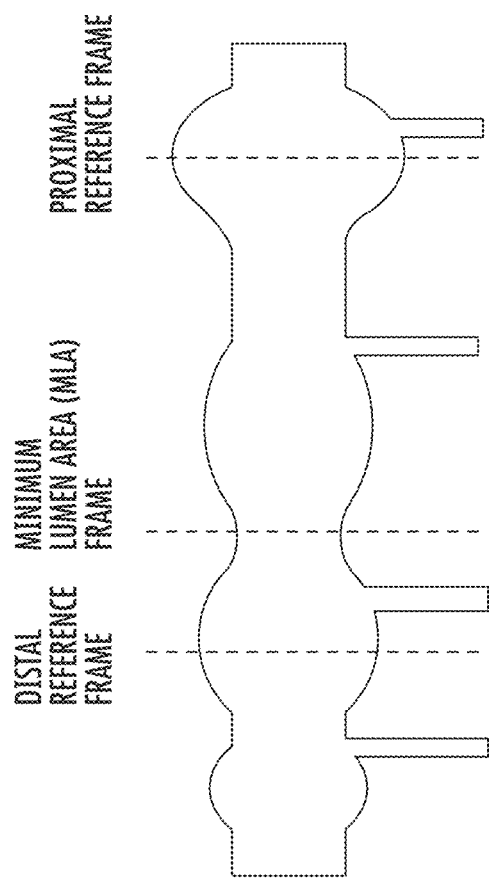
FIG. 3 is an example of a highly schematic representation of mean-diameter profile of a longitudinal cross section used to determine stenting.

The invention builds on methods disclosed in the patent application (US Patent Publication No. 2011/0071404) for constructing a mean-diameter profile of a branched vessel via automated processing of intravascular images. This prior application is incorporated herein by reference in its entirety. FIG. 3 is an embodiment of a simplified version of a display of the mean-diameter of the lumen known to the prior art. The solid black regions show variations in the mean diameter of the lumen of the vessel segment, as well as the longitudinal positions and diameters of the side branches within the segment. The horizontal axis represents the image frame number, which corresponds to the distance along the axis of the vessel.

In one embodiment, the image frame at which the lumen area is a minimum (the MLA cross section) serves as a marker for measurement of the percent area stenosis relative to the cross-sectional area measured at one or more reference frames. The reference diameters are intended to represent the diameters of the lumen in segments of the vessel that are acceptable points of contact between the vessel and the edges of the stent. The best points of contact are those regions of the artery where lumen area is a local maximum and where plaque is minimal (i.e., the intima is thin and uniform).

Although a display of the mean diameter profile provides a useful guide for stenting of an artery, this type of display does not distinguish between normal and diseased segments. Further, the mean diameter profile display does not provide a reliable indication of the natural tapering of the vessel. That is, the diameters of blood vessels typically taper as one proceeds along the vessel away from the heart. To locate suitable normal reference cross sections, the user must still search manually through the set of image frames within the regions where the diameter is largest to choose the best candidates. Once suitable reference frames have been located, a rough measure of the amount of tapering in the vessel can be obtained from the difference between the mean diameters measured at a pair of reference frames located proximally and distally to the MLA frame respectively. Unfortunately, many times only a single reference cross section can be found, so the degree of vessel tapering within the target segment cannot be measured. The locations of the branches shown in the mean-diameter profile are helpful for placement of the stent, but the effect of the branches on vessel tapering cannot be discerned easily.

The intent of the invention disclosed herein is to simplify stent planning, evaluation and adjustment by automating the procedures for determining the optimum lumen contour of a stented vessel. This optimum contour is intended to serve as an objective guide for stent sizing, deployment, and post-stent evaluation. Determination of the optimum lumen contour is based on quantitative image-processing methods that account for plaque thickness, size and location of side branches, and vessel tapering. Various embodiments of the invention extend the utility of OCT- or IVUS-derived mean diameter data by eliminating manual operations involved in the selection of the normal reference cross sections and the estimation of the tapered normal vessel profile for stent sizing.

Figure 4:
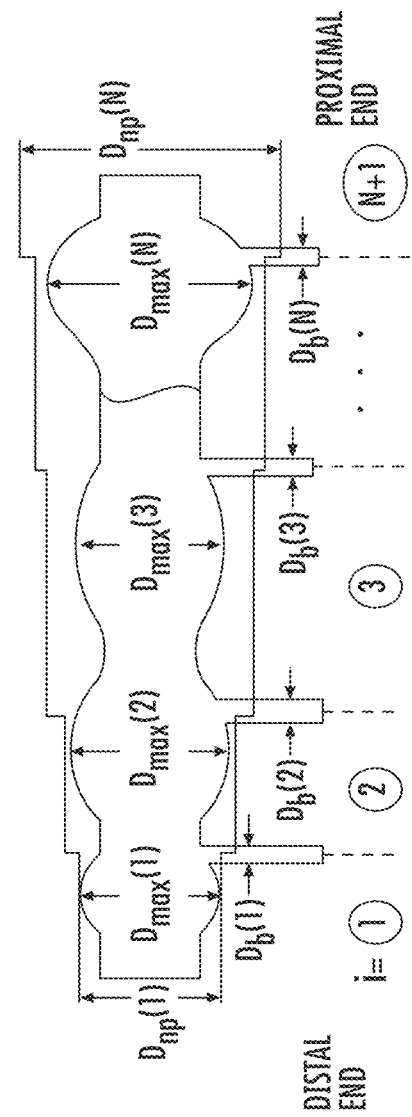
FIG. 4 is an embodiment of a mean diameter profile with inter-branch segmentation and associated notations for automated analysis of vessel lumen contours according to the invention.

Referring to FIG. 4, generally one embodiment of the method divides the vessel into a plurality of (N) segments. Each segment is defined as the space between the branches of the vessel. In FIG. 4, each branch of the vessel is shown as a vertical line extending downward from the vessel regardless of the actual orientation of the branch around the circumference of the vessel. Branch locations and diameters are determined by software algorithms that automatically locate and measure discontinuities in the circumference of the lumen contour of vessel cross sections. The method then uses a starting point, for example, the most distal segment (1) of the vessel in the general area in which the stent is intended to be placed that appears to be substantially unstenosed. The current maximum diameter $D_{max}(1)$ is assumed to be defined at this location.

The method then evaluates the next segment (2), in this case the adjacent proximal segment, and calculates what the maximal diameter of the next proximal segment (2) should be, given the diameter of the present segment, the diameter of the branch between the segments and knowledge that the vessel tapers according to a power rule as described below. The actual diameter of the next proximal segment is measured and whichever diameter (measured or calculated) is larger is used as the maximum diameter of this next segment $D_{max}(2)$. The process then proceeds to the next proximal segment and so on until the entire length of the vessel in which the stent is to be placed is examined. At this point, the expanded diameters of both ends of the stent are defined.

Another embodiment is similar to the previously discussed embodiment except that the quality (degree of severity of disease) of the maximum diameter is determined. If the segment having the maximum diameter within a segment appears to be diseased, other image frames within that segment are examined and the less diseased frame is chosen for the maximum diameter. In this way, the maximum diameter frame used may actually have a smaller physical diameter but may also have a smaller diseased portion of the lumen, and so is more likely to be indicative of the actual lumen diameter.

In more detail, as stated above, natural lumen tapering is assumed to result primarily from branching of the coronary artery, in accordance with a power scaling rule derived from the analysis of blood flow in the coronary vasculature. This rule states:

$$D^\varepsilon(i+1) = D^\varepsilon(i) + D_b^\varepsilon(i) \quad \text{[Eqn. 1]}$$

where D(i) and D(i+1) are the lumen diameters in the vessel segments distal and proximal, respectively, to the ith branch. The ith side branch has a diameter $D_b(i)$. The exponent & is a power-law scaling exponent which has a value between about 2 and about 3.0 as determined empirically. Selection of the best value of & is based on statistical analysis of OCT and angiographic image databases in which the tapering of the vessels and the branch diameters of those vessels are measured. In normal patients, the value is typically about 2.5

Referring again to FIG. 4, in one embodiment of the present method the image of the vessel, composed of a plurality of frames, is divided into N+1 inter-branch segments, where N is the number of side branches. Each of the plurality of frames within a segment corresponds to a cross section of the segment. The mean diameter of each inter-branch segment is then determined by examining the frames that make up the segment. The image frame in each segment in which the lumen diameter equals the maximum for that segment becomes a candidate for the normal reference segment, that is, the largest diameter in the vessel without stenosis. Boundary tracing methods, such as described in US Patent Publication No. 2011/0071404, when applied to the raw intravascular image data, can be used to measure the mean lumen and branch diameters automatically.

Briefly, one embodiment of the boundary tracing method to detect the lumen of a vessel first includes making an image mask to demark the general contour of the lumen wall. In one embodiment, the mask is binary. The mask is made of a plurality of scanlines, with each scanline defining the beginning and end of a tissue area. Because it is possible that a scanline may include more than one region of tissue, due to blood artifacts etc., a weight is associated with each region of tissue. Next, a list of weighted tissue is created and potential contours defined. In one embodiment, the longest contour segment is defined as the root contour segment. The next adjacent contour segments, both clockwise and counter-clockwise, are then identified.

A valid next contour segment is one that passes both angular, radial and Euclidian distance and length thresholds. That is, its angular extent must be greater than a certain threshold; its radial position must be similar to the other segments; and its direct connection distance (Euclidian distance) to the next adjacent contour segment must be greater than a certain threshold. Finally, the lengths of the potential contour segments are determined and the one with the longest length selected as an actual contour segment. Missing contour data between contour segments is then interpolated to remove the gaps in the contour. At this point, a full contour of the lumen has been defined in each frame of a given vessel segment.

There are two situations which can now arise, corresponding to the two embodiments of the method described generally above. In one situation, there is insufficient or no information about the vessel such that a normal or non-diseased region cannot be defined. In the other situation, the vessel includes both plaque damaged and normal tissue areas.

One specific embodiment of the invention applies to the first situation when no information about the characteristics of the plaque in the wall is available for determining the degree of normality of particular vessel segments. This case may arise when the imaging modality is unable to distinguish diseased and normal tissue or when imaging quality has been degraded.

Figure 5:
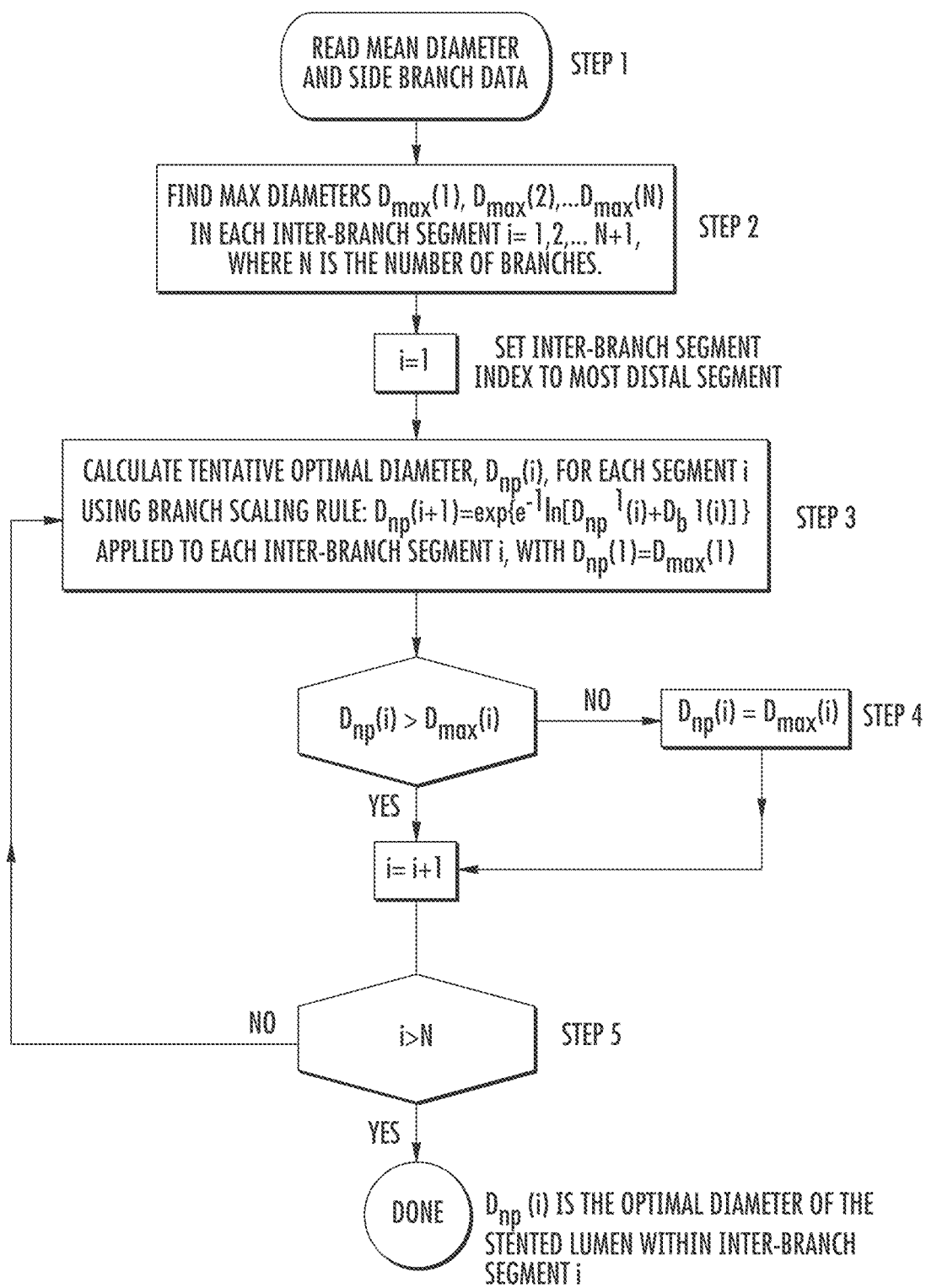
FIG. 5 is a flow chart that outlines an embodiment of a procedure for determining optimal stented contours of stenosed blood vessels when no information is available about the characteristics of the plaque in the wall of the vessel.

Referring to FIG. 5, the flowchart shows one embodiment of the computations and decisions used to determine the optimum stented profile of the vessel when no information about normal vessel diameters is available. One feature of the method shown is that the method is designed to prevent overexpansion of the stent while still incorporating information from all inter-branch segments. First, the mean diameter of each segment and side branch is measured. (Step 1). The mean diameter is the diameter of a circle which has the same area as that of the cross section of the vessel at that location in the segment.

As a starting condition, the maximum mean diameter ($D_{max}(1)$) as measured using the OCT image in the most distal segment of the vessel image (the segment given the designated index (i=1)) is defined as the optimal distal normal reference diameter (np): $D_{np}(1) = D_{max}(1)$ (Step 2). From this point, the optimal diameter of each of the (N+1) segments from distal to proximal is calculated using the power scaling rule of Eqn. 1 in the form shown in Eqn. 2 (Step 3).

$$D_{np}(i+1) = \exp\{(1/\varepsilon)\ln[D_{np}^\varepsilon(i) + D_b^\varepsilon(i)]\} \quad \text{[Eqn. 2]}$$

However, if the calculated optimal stented diameter in the next adjacent proximal segment, $D_{np}(i+1)$ is less than the measured maximum diameter of segment (i+1), then the next adjacent proximal segment (i+1) is set to $D_{max}(i+1)$ (Step 4). That is:

$$\text{IF } D_{np}(i+1) < D_{max}(i+1)] \text{ THEN } D_{np}(i+1) = D_{max}(i+1) \quad \text{[Eqn. 3]}$$

The iterative process of the calculation according to Eqn. 2, with Eqn. 3 as a condition, repeats until all segments are evaluated (Step 5). The condition described by Eqn. 3 is included to compensate for errors in the scaled diameters that result from branches narrowed by ostial disease, especially in regions where plaque burden is heavy The second embodiment of the invention discussed above applies to the more general case in which the degree of normality of particular vessel segments is rated according to the plaque thickness and other variables derived from the intravascular data by a separate image-processing algorithm. In one embodiment of the method, the rating scheme assigns an integer on a scale between 1 and K to each image frame, where 1 indicates normal (not diseased) and K indicates not normal (heavily diseased). K is typically a small integer between 2 and 5. Only non-diseased image cross sections with a very thin intima (less than a few hundred micrometers thick) over their entire circumference are assigned a rating of 1.

Diseased cross sections are assigned higher numbers up to the maximum value K in accordance with the thickness of the intimal layers and the angular extent of the intimal thickening. For example, the intima can appear thin with no significant plaque over, for example, 90° of circumferential arc of the vessel cross section and thick (due to presence of plaque) over the remaining 270°. This cross section would be given a higher numerical rating (more diseased) than a vessel with a thin intima over, for example, 180° and thick over the remaining 180° of circumference. Specific methods for calculating these ratings from OCT image data are described herein.

Figure 6:
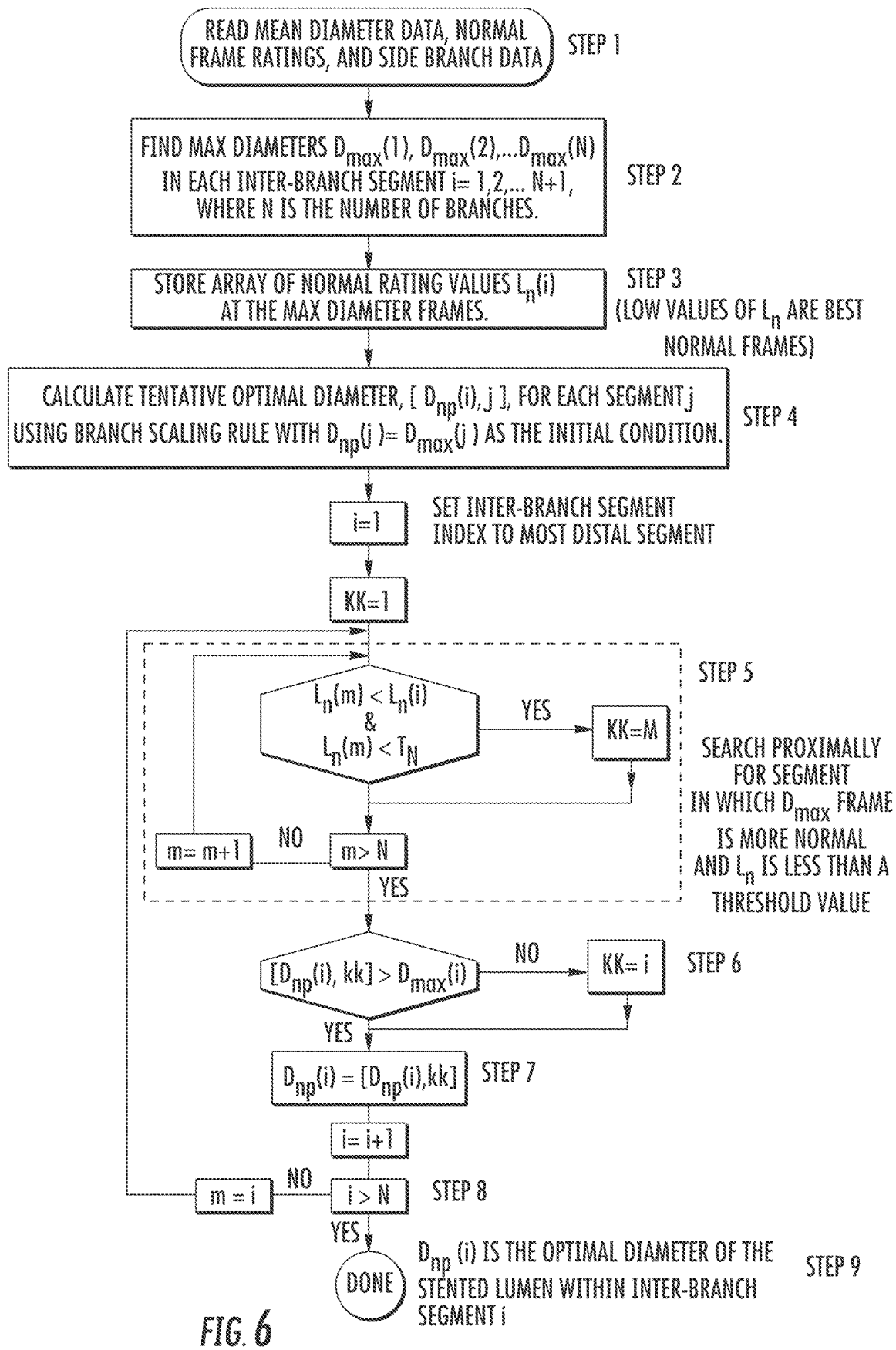
FIG. 6 is a flow chart that outlines another embodiment of a procedure for determining optimal stented contours of stenosed blood vessels when information is available about the characteristics of the plaque in the wall of the vessel.

FIG. 6 is a flow chart for the process of determining the optimum stented lumen contour according to the embodiment of the invention described above, which uses a normality rating of:

$$1 \leq L_n \leq K$$

for each image cross section. In this embodiment, (i) again indicates segment number, mm is the counting index, kk is the stored index and N is the total number of segments. As in the previous embodiment, the computations begin with the most distal frame and the optimal diameters are determined by the scaling rule described by Eqn. 1. However, the inclusion of the normality rating permits expansion of the stent in a distal segment beyond the maximum diameter measured in the current segment, if the normality rating $L_n$ in a nearby cross section is lower. The best reference diameter for a given segment is chosen as the maximum diameter in the closest proximal segment with a better normality rating. The maximum diameter condition is included to compensate for errors in the scaled diameters that result from branches narrowed by ostial disease.

This method of using normality begins, as in the other embodiment, by acquiring the mean diameter of the segments and the side branch data (Step 1). The maximum diameter for each inter-branch segment is determined next (Step 2). A normality rating is determined at each of the maximum diameter frames (Step 3). The tentative optimal diameter is then determined (Step 4). At this point, a search is made proximally for a segment in which the $D_{max}$ is more normal and the normality rating, $L_n$ is less than a predetermined threshold (Step 5). Each segment is searched for the maximum diameter (Step 6). When the frame having a maximum diameter greater than the previous maximum diameter is located, it becomes the new optimum diameter (Step 7). After all the frames are searched (Step 8), the optimal diameter within the segment is determined (Step 9). After all the segments are searched, the optimal diameter for the stented lumen within the vessel has been determined.

Figure 7:
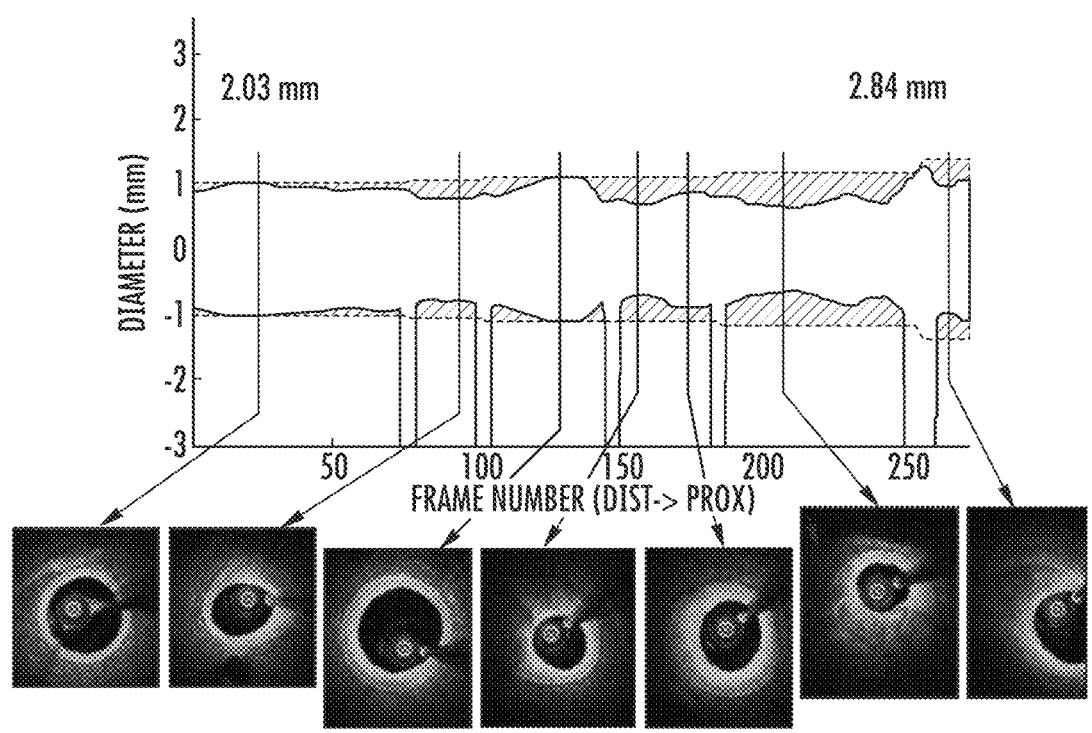
FIG. 7 shows an embodiment of an optimal lumen contour which was derived from OCT data in accordance with the embodiment of the invention shown in FIG. 6.

FIG. 7 shows an example of an optimal lumen contour that was derived from OCT data in accordance with embodiment of the invention described in FIG. 6. The area shown hatched is intended to serve as a guide for choosing the diameter and length of the stent. A cross-sectional OCT image at each of the maximum mean-diameter frames is shown for reference. In this example, the lumen diameter tapers relatively smoothly from a mean of about 2.84 mm to about 2.03 mm, with a moderate step in diameter at the proximal end of the vessel segment due to the presence of a side branch centered on frame 255. Good conformance is evident between the computed contour and the lumen diameters of the cross sections in which the vessel intima is thinnest. For a frame spacing of about 0.2 mm, the stent length needed to cover the most severe portion of the lesion is approximately 27 mm; that is, from image frame 125 to image frame 260.

In one embodiment, the user may select locations on the computed contour for setting the preferred contact locations for of the edges of the stent. To facilitate planning of the contact locations, the regions of the image with high normality ratings are displayed in some embodiments as color-coded bars or other indicators. The reference frame detection and rating method uses image processing and computer vision algorithms to determine the thickness of the intima-media (IM) and the outer adventitial (OA) regions. This is done using a combination of approaches that work directly on the raw A-line, scan data from the center of the image outward, and the reconstructed frame. In one embodiment, the system warns the user if the distal contact point is not in a substantially normal region of the vessel.

Figure 8A:
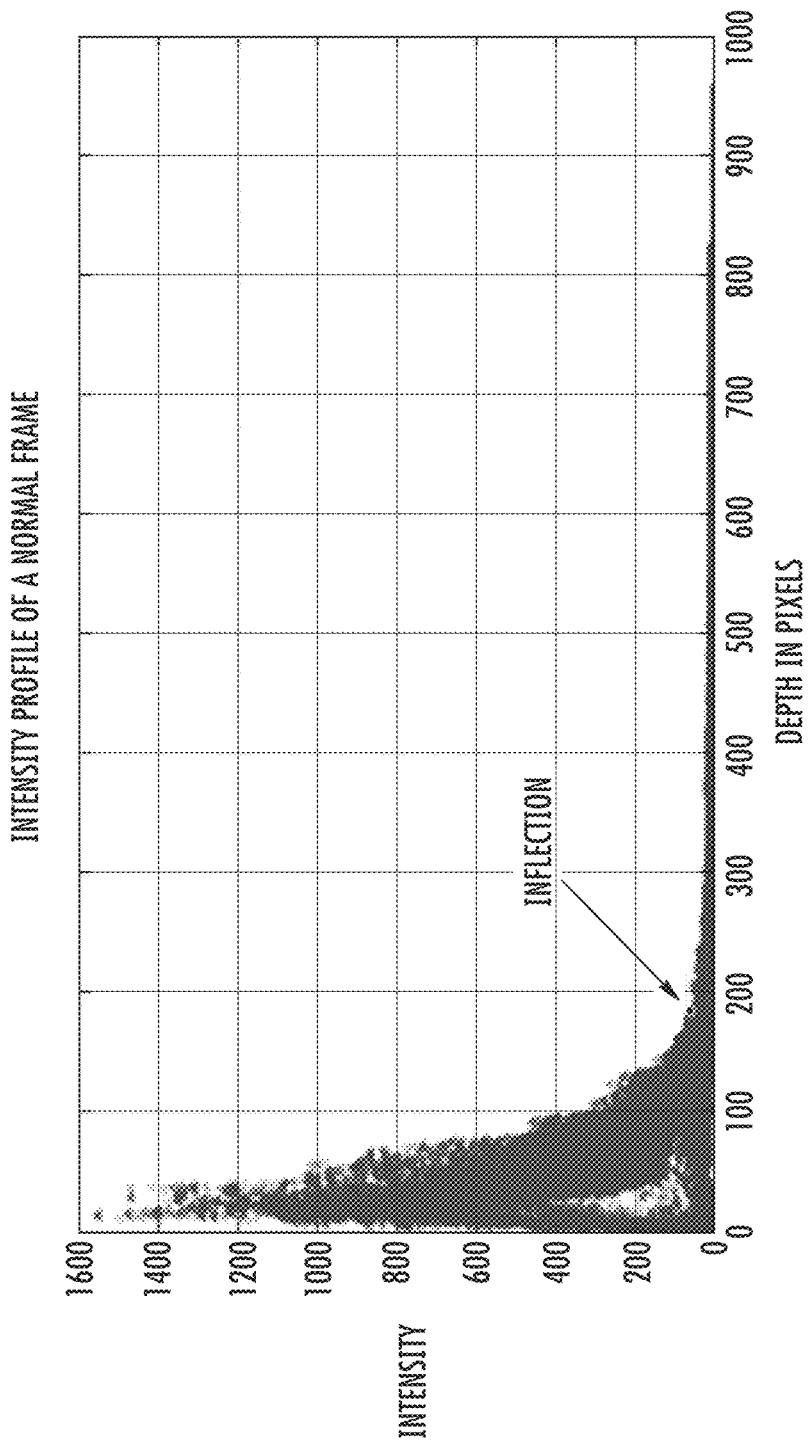
FIGS. 8a and b are plots of intensity against pixel depth for an image frame of a normal vessel and a vessel with plaque, respectively, obtained according to an embodiment of the invention.
Figure 8B:
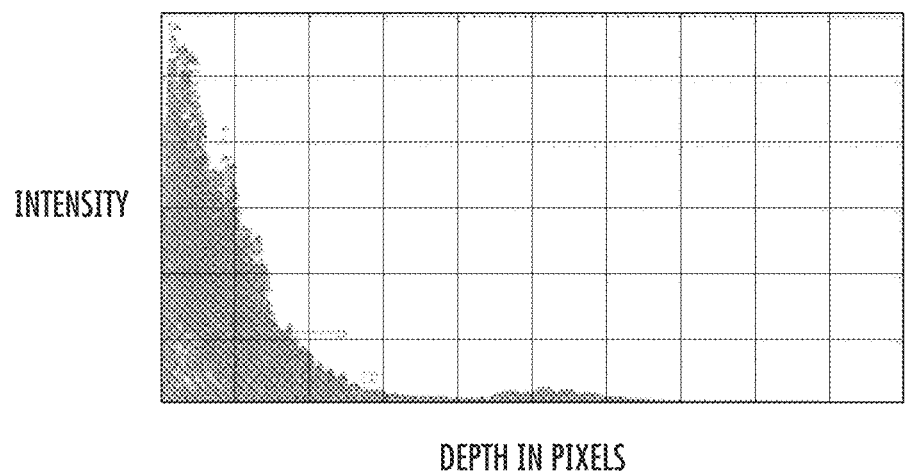

One approach to defining normality is to determine an optical threshold. In one embodiment, an optimal intensity threshold is determined based on the combined image intensity profile along all of the A-lines in each frame. The threshold is chosen such that it is at the region of inflection shown by the arrow in the intensity profile of the A-line (FIG. 8*a*). This threshold can also be determined by computing the mean intensity value corresponding to a region at a fixed distance (e.g., about 0.56 mm) from the lumen wall. This distance corresponds to the intima-media (IM) region as measured in histology studies. For frames with plaque, there is a thickening of the intensity profile (FIG. 8*b*), which appropriately modifies the threshold value. An intensity threshold value that is within a tolerance factor of the inflection point is used to create a binary image with foreground and background separated. The foreground of the binary image corresponds to the IM region, whose thickness is measured. The average thickness of the IM region indicates the degree of normality. Frames with plaque have a thickened IM region while normal, non-diseased frames have a uniform small IM thickness.

Another approach is to consider that a reference frame with no disease has a uniform texture and intensity characteristics for all A-lines in the frame. This uniformity characteristic is captured using both cross-correlation and structure similarity techniques. Each A-line and its neighboring A-lines are grouped together to create what is termed an A-line patch. The patch is then cross-correlated, using normalized cross-correlation, with the entire A-line data set and the correlation numbers combined. This process is repeated with the next overlapping A-line patch until every A-line patch is cross-correlated across the entire A-line data.

Figure 9A:
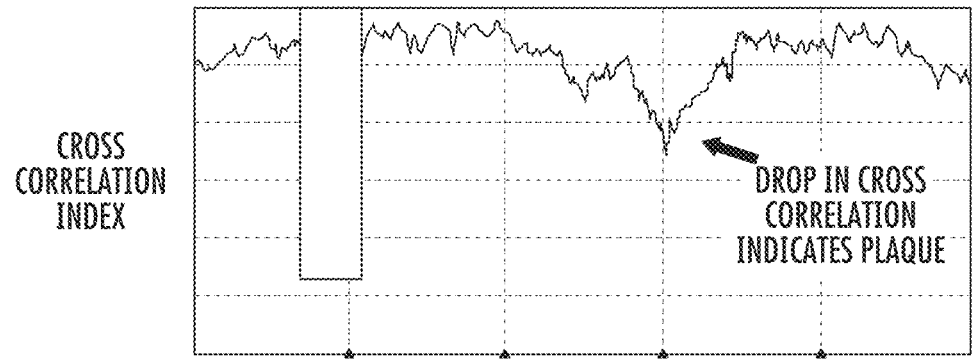
FIG. 9a is a plot of the correlation of an A-line patch with the A-line data set obtained according to an embodiment of the invention.
Figure 9B:
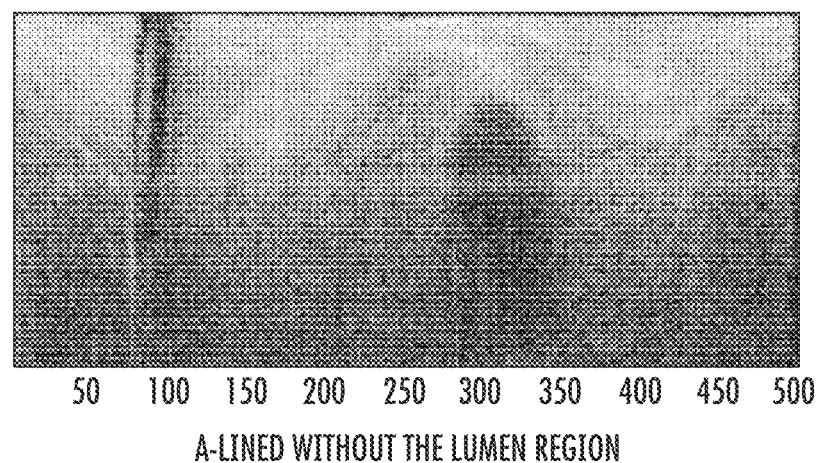

The correlation numbers are then plotted (FIG. 9). A-lines that have a lower correlation number compared to neighboring A-lines indicate non-uniformity, implying the presence of plaque. A normal non-plaque frame will ideally have a uniform correlation number across all A-lines. The blackened area in the graph corresponds to the region of guidewire shadow. A structure similarity metric (SSIM) such as that of Z. Wang et al. in "*Image quality assessment: From error visibility to structural similarity*", *IEEE Trans. Image Proc*, vol 14, no 4, 2004 which measures intensity similarity along with cross-correlation will also provide uniformity characteristics that can be used to distinguish between normal and diseased frames. The Wang approach uses the mean and standard deviation of intensities in a window centered at each pixel in two adjacent patches to compute a metric for perceptual change in the structure between the two patches. Frames that have a more uniform SSIM across all patches tend to be normal while those with plaque will have non-uniform SSIM values.

Another measure of normality is the IM to OA ratio. To obtain this ratio, the frames of interest are first filtered using a filter bank that consists of a combination low pass and Gabor filters. A basic Gabor filter (Eqn. 4) is a Gaussian filter modulated with a sinusoid function. It behaves as a bandpass filter and can be oriented in different radial directions around the vessel image. The Gaussian is directed along different predetermined orientations by varying the phase term in the equation below, to capture the characteristic specular regions that are seen in the OA regions of normal frames. The general form of the filter is:

$$g(x, y) = \exp\left\{-\frac{1}{2}\left[\frac{x^2}{\sigma_x^2} + \frac{y^2}{\sigma_y^2}\right]\right\}\cos(2\pi\mu_0 x + \varphi) \quad \text{[Eqn. 4]}$$

where $\mu_o$ is the frequency, $\varphi$ is the phase, and $\sigma_x$ and $\sigma_y$ are the Gaussian envelope parameters. Through the selection of x and y, Gabor filters with arbitrary orientations are obtained. Gabor filter banks have been used extensively in segmentation and pattern recognition applications, particularly for texture classification. The optimal set of filter parameters for the filter bank is obtained through a training process that identifies the range of parameters that highlight the specular characteristics, especially the angular and size-intensity variation of the OA region.

In one embodiment, for training, a set of OA regions is identified by the user and a Gabor filter is applied to the set. The filter parameters, such as the $\varphi$, $\sigma_x$ and $\sigma_y$ are varied across a wide range of values. The set of parameters that give the largest response to the OA region, with a low response to the IM region, is selected as the best set of parameters to filter the OA region. Once these optimal parameters are determined, they can be used for all datasets. A major distinguishing characteristic between the IM and OA region in normal frames is the presence of specular features indicating the presence of loose collagen or perivascular fat in the adventitia. The filter, once tuned, attempts to highlight these features while suppressing all others.

After filtering the frame using the filter bank described above, the resulting IM region and the specular OA region are highlighted with high intensity color compared to the background. In the next step, two sets of contours are developed on the filtered image; one from the center of the image outward, and the other from the outside boundary of the image inward. That is, two sets of contours are being developed, one attempting to define the boundary between the IM and the OA moving from the center outward, and one moving from the outside inward. The contour propagates based on the underlying image intensity and texture characteristics. The image is filtered, highlighting the IM and OA texture. The IM contour propagates with a constant speed when the underlying region has homogeneous texture, characteristic of the IM region. It slows and stops its propagation when it reaches regions with texture characteristic of the OA region. The OA contour, which starts from the outer boundary of the image, propagates through noise until it reaches the OA texture region, at which point it slows and stops.

Figure 10A:
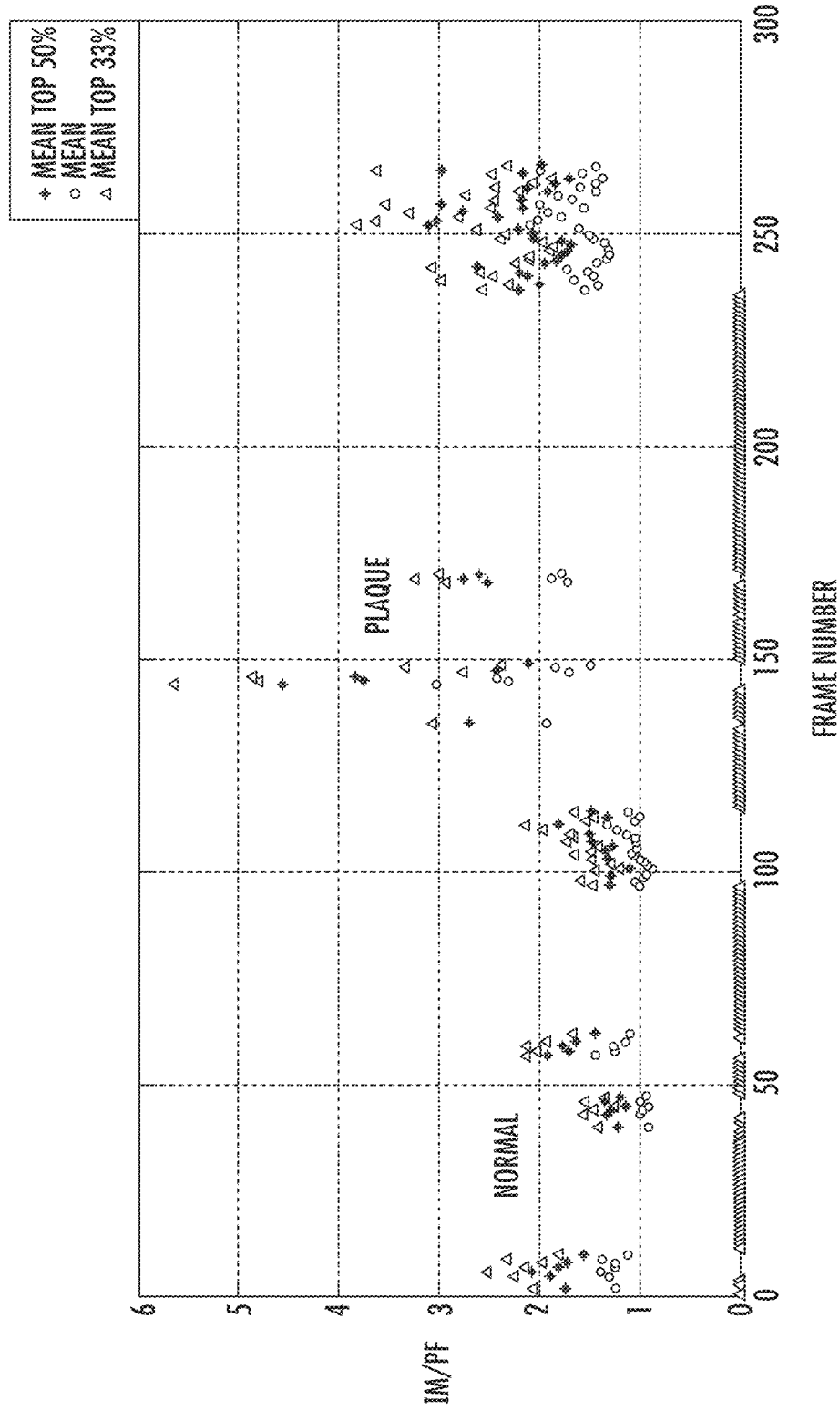
FIG. 10a is a plot of the ratio of IM (intima media) to OA (outer adventitia) for each frame obtained according to an embodiment of the invention.

The inner contour is propagated outward from the lumen boundary, which has already been detected by standard OCT software. The step size for the propagation of this contour at each point is determined based on the underlying intensity characteristics at that point in the image; a bright uniform region implies large step, while low intensity and high intensity gradients imply a small step size. The contour stops propagating when it reaches an edge gradient that corresponds to the edge of the IM region. FIG. 10C depicts the IM and OA regions.

The outer contour is propagated towards the center from the outer edge of the image. As with the inner contour, each step of this contour is based on the underlying intensity characteristics. Here, the step size is large when the intensity value is low and the contour stops propagating when it reaches an edge or a high intensity region. This will typically correspond to the edge of the OA region. The outer contour is grown after the inner contour has finished evolving. If the outer contour comes close to the inner contour, which occurs when there are insufficient filtered specular features in the OA region (something that happens typically in plaque), its propagation is terminated. The region between the inner and outer contour corresponds to the segmented OA region. Frames with plaque will have thinner OA region while those without plaque, having strong specular features highlighted after the texture filtering step, will be thicker.

Figure 10B:
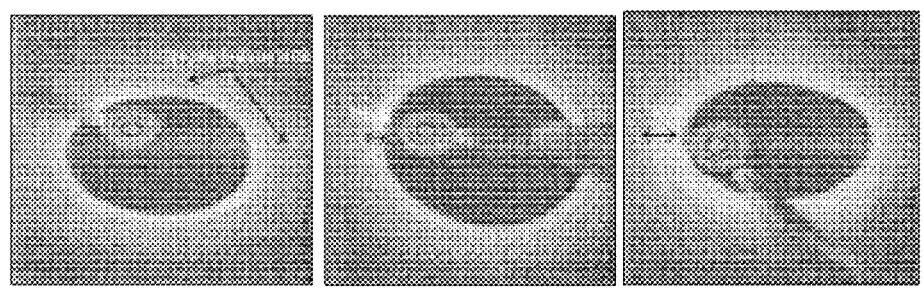
FIG. 10b is a series of images corresponding to various frames shown in the plot of FIG. 10a obtained according to an embodiment of the invention.
Figure 10C:
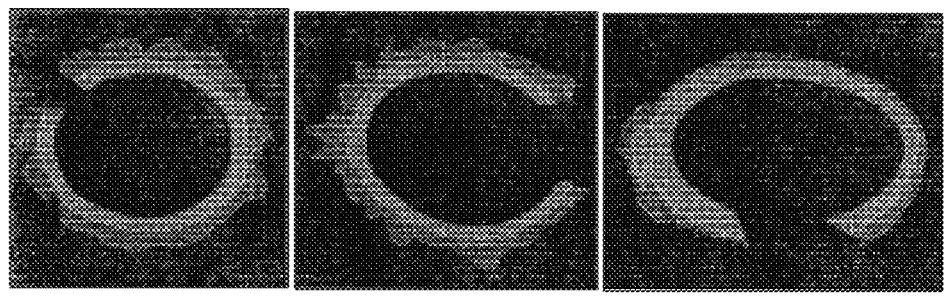
FIG. 10C are the images of FIG. 10b processed according to an embodiment of the invention.

The two contours thereby create a partition or segmentation of the frame into IM and OA region (FIG. 10b). The ratio of the IM width to the OA width at each A-line provides an indication of normality (FIG. 10a). Plaque regions have a high IM and a very low OA region, while normal regions have an almost equal IM and OA width. The mean ratio for all A-lines in the frame, ignoring the guide wire region, is an indication of normality as exemplified by the clustering in FIG. 10a. Frames which have no plaque have low mean IM to OA ratio while those with plaque have large IM to OA ratio.

In more detail, FIG. 10a shows a scatter plot of the mean IM to OA ratio for a sampling of frames. A scatter of the mean of the top 50% of the IM to OA ratio and the top 33% of the IM to OA ratio are also plotted. Frames that have an IM to OA mean ratio greater than about 2 are diseased, while those below about 2 are normal. These frames with a ratio of less than about 2 are used as reference frames. The various mean ratios provide a measure of normality that is used as a rating for the reference frames. In FIG. 10c, the frames at the bottom are the output of the filtering and contour growing steps and show a partitioning of IM and OA. This is used to compute the IM to OA ratio for that frame. The frame with plaque shows a smaller OA thickness overall, hence its IM to OA ratio is much higher than the frames which do not have plaque.

Figure 11A:
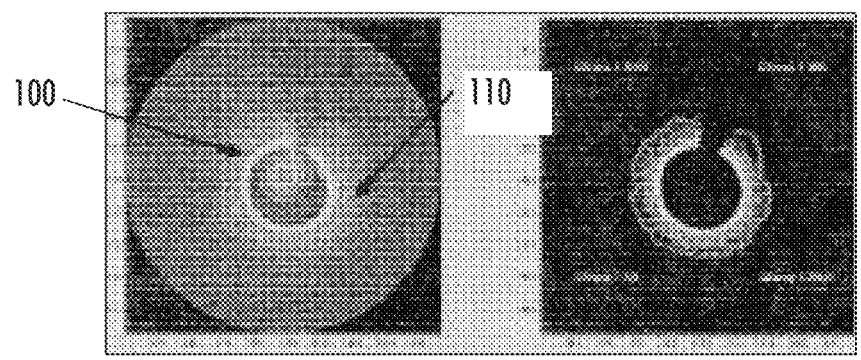
FIG. 11a is an image of normal tissue which is defined as a normal reference frame according to an embodiment of the invention.
Figure 11B:
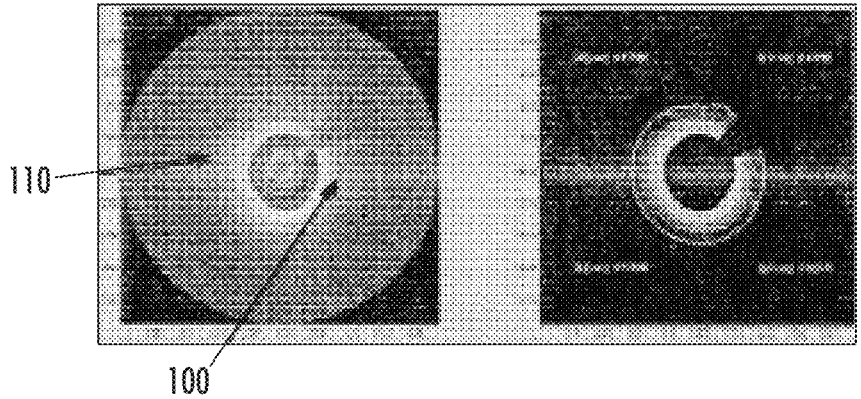
FIG. 11b is an image of diseased tissue which is defined as a diseased frame according to an embodiment of the invention.

In one embodiment, a rating of 1 to 5 is provided for each frame, where 1 indicates an image frame of normal tissue and 5 indicates an image frame of diseased tissue. The rating is based on the number of quadrants in which the IM region has a thickness above a certain threshold. The frame shown in FIG. 11a is rated 1, while the one in FIG. 11b is rated 5. The inner 100 and outer 110 contours are the inner and outer contours that segment the IM and OA regions. The average IM thickness in each quadrant is calculated based on the inner contour. A thick IM in all quadrants indicates disease, and is given a lower rating.

Figure 12:
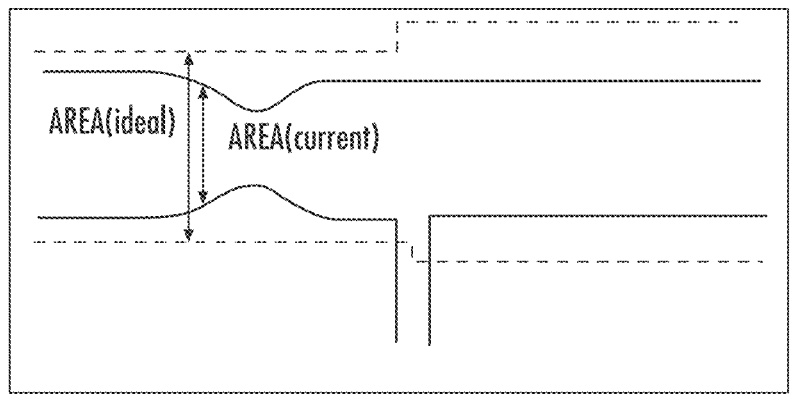
FIG. 12 is a schematic diagram showing the points of measurement for calculating the stent expansion index according to an embodiment of the invention.
Figure 13:
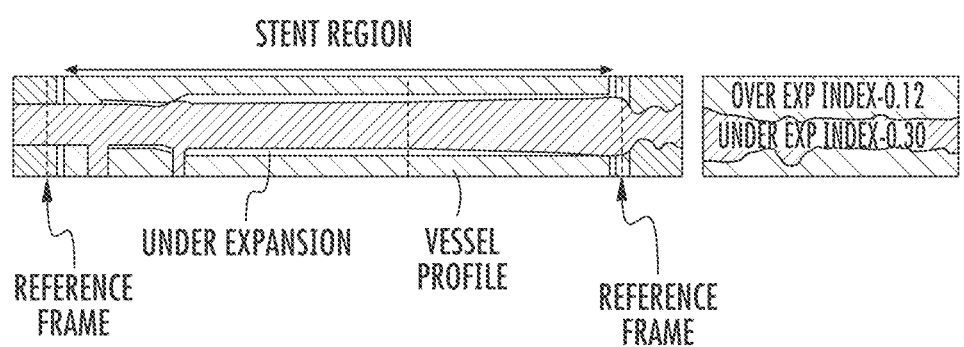
FIG. 13 is a schematic diagram of a stented region showing the use of expansion indices.

The computed stent profile is compared with the lumen diameter to determine an index value that provides a measure of error or deviation between the computed ideal profile and the current lumen profile (see FIGS. 12 and 13). At each frame, the percentage difference between the computed stent profile area and the current lumen area is calculated.

$$\text{Stent expansion error index} = (\text{AreaIdeal} - \text{Areacurrent})/\text{Areacurrent} \quad \text{Eqn. 5}$$

The error computed at each frame is combined to give a single index for the entire pullback. A lower number will indicate a smaller error (FIG. 13).

Figure 14:
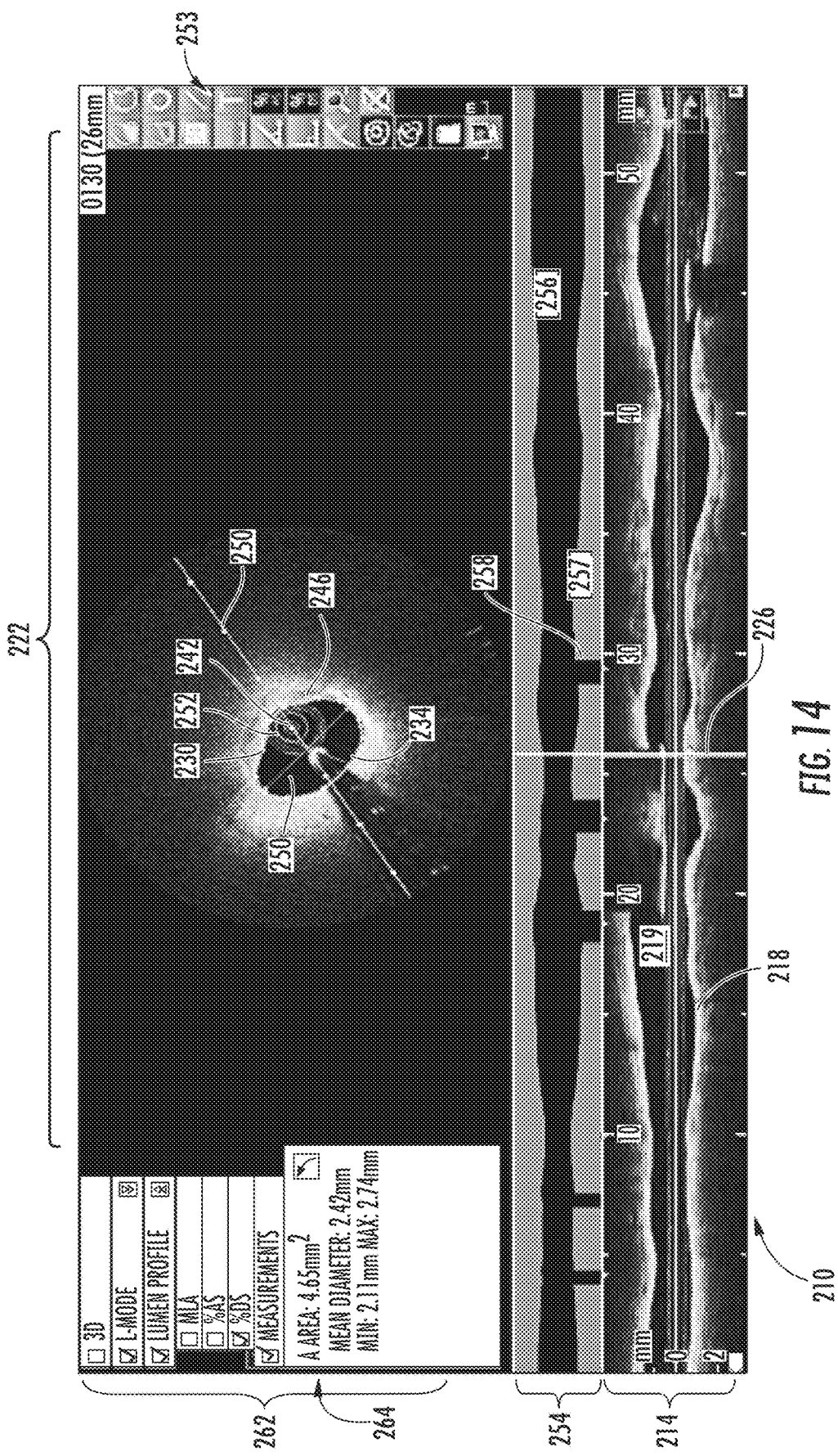
FIG. 14 is a screen shot of an embodiment of a graphic interface of the system.

Referring to FIG. 14, an embodiment of the graphic interface 210 of the system includes a number of panels or subscreens. The first panel 214 is a longitudinal section of the vessel being imaged by OCT. The light areas 218 denote the walls of the vessel lumen, while the black area 219 is the lumen of the vessel. The second panel 222 is a cross section of the vessel shown at the location in the first panel 214 indicated by the white vertical line 226.

The vessel lumen, as detected by the system or a component thereof, is indicated by the dotted segmented boundary 230. The shadow 234 in the image is the shadow caused by a guidewire used to direct the probe. The center of the probe 238 is imaged as the white dot 242 surrounded by concentric circles. The brightest concentric circle 246 is a titanium oxide calibration layer within the wall of the probe. The diagonal line with dots 250 represents the orientation of the image cut plane through the longitudinal axis of the vessel. The maximum 251 and minimum 252 diameters are displayed. In addition, a series of control boxes 253 are displayed that allow the operator to manipulate the image in various ways.

The third panel 254 is a silhouette representation of the lumen of the vessel in which the interior of the lumen is in darker [256] and the exterior of the lumen is in lighter [257]. The vertical black regions 258 (only one labeled for clarity) or bars are side branches, which, regardless of their actual orientation as they leave the lumen, are depicted depending vertically from the lumen. The width of a vertical black region is a measure of the width of the side branch.

The fourth panel 262 is an information panel which indicates what is being shown and any measurements made on the lumen image in the second panel 222. In this example 264, the area of the lumen is calculated and the maximum and minimum diameter measurements displayed.

Figure 15:
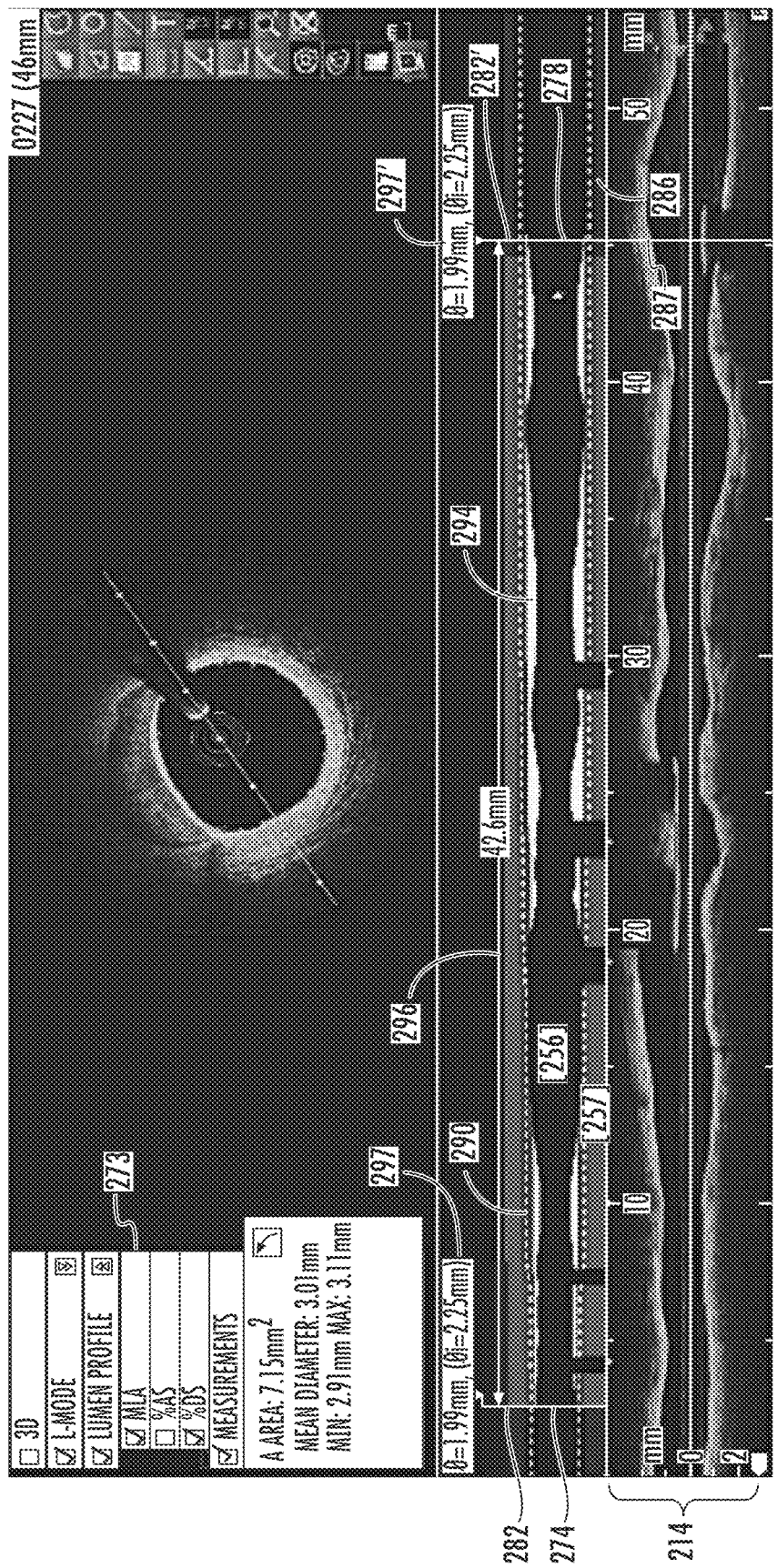
FIG. 15 is a screen shot of the graphic interface of the system shown in FIG. 14 with a section of lumen selected for stent placement.

Referring to FIG. 15, in this example the user has moved the cross section location indicator (shown as line 287 at about 45 mm in the cross section frame 214) and has indicated that the MLA is to be calculated by checking the MLA box 273 in panel four. In response, the system generates a distal boundary marker 274 and a proximal boundary marker 278 and allows the user to position each of those lines separately, where desired, by dragging and dropping each line. Panel three indicates where the distal and proximal boundaries are located 282, 283 and displays the target lumen diameter for a given lumen region (white hashed lines) 286. The target lumen diameter is largest the size of the vessel that should not be exceeded by a stent diameter because of the possibility of rupturing the vessel. Note that as the lumen decreases at side branches, the white hashed lines step-down (see for example, 290) at a branch. In addition, the system shades in region 294, such as with hatching or a contrasting color, as the difference between the actual lumen wall and the target lumen diameter shown with the hashed white line. The system displays the distance between the proximal boundary and the distal boundary indicators 296. Thus, in one embodiment the software can be configured such that as part of a given user interface a difference between an actual lumen wall and a target lumen diameter is displayed using a visual indicator.

Figure 16:
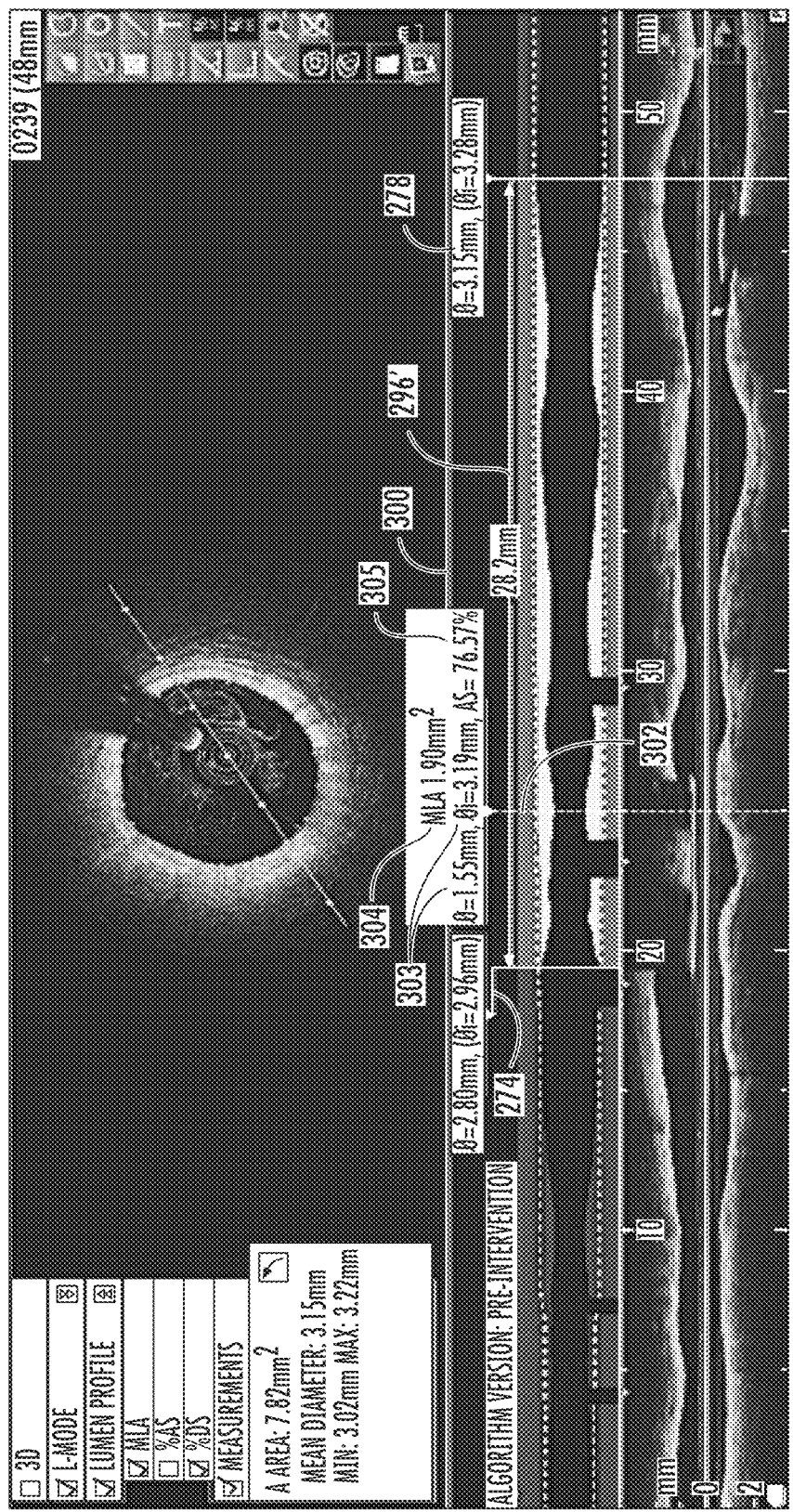
FIG. 16 is a screen shot of the graphic interface of the system shown in FIG. 14 with another section of lumen selected for stent placement.
Figure 17:
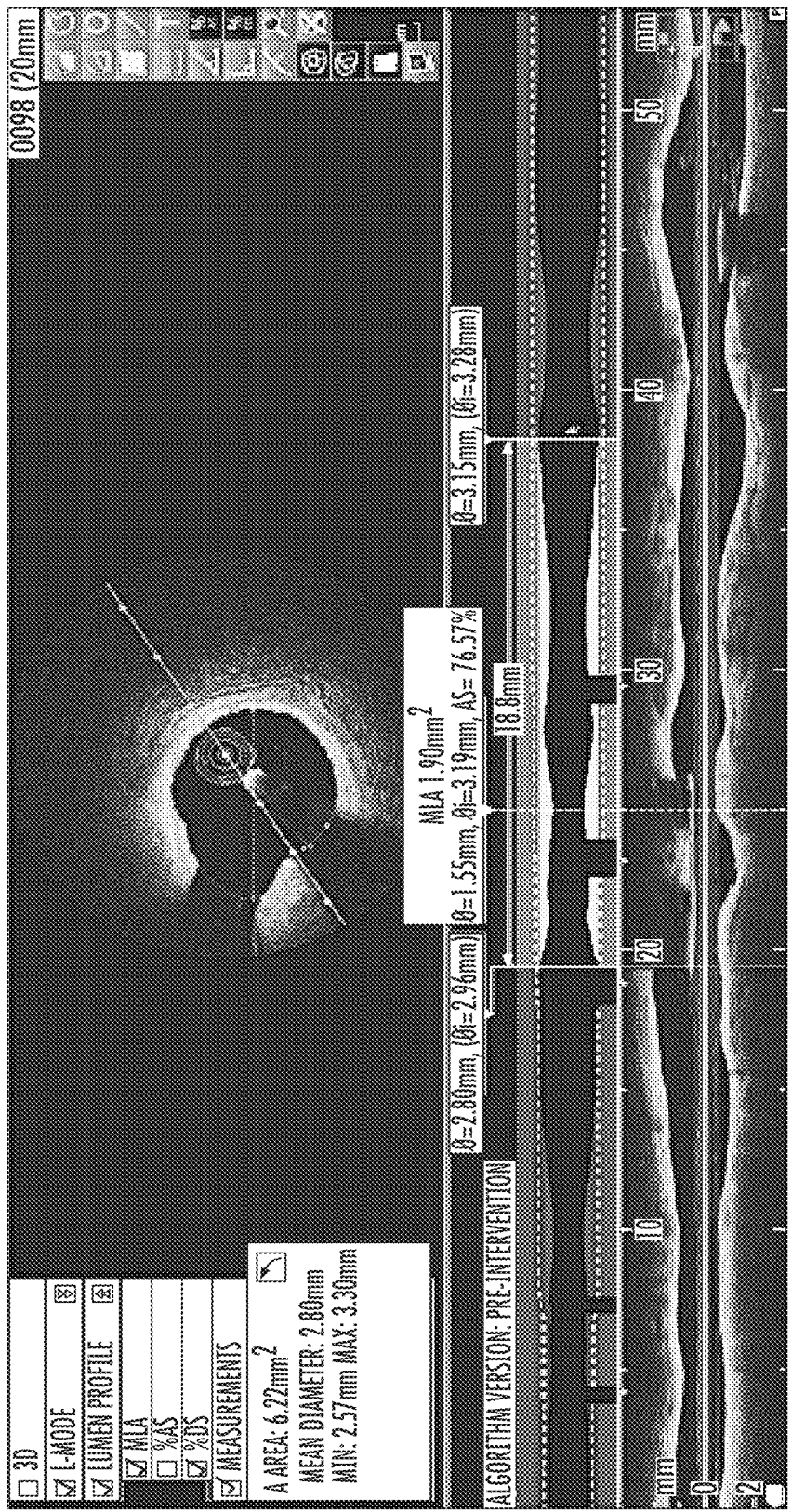
FIG. 17 is a screen shot of the graphic interface of the system shown in FIG. 14 with yet another section of lumen selected for stent placement.

Referring to FIG. 16, as shown, the user has moved the lower 274 and upper 278 boundary markers and the system has recalculated the MLA for this new range and displayed it 300 in the panel. In addition, the system recalculates the difference between the distal and proximal boundary indicators and displays this measurement 296'. The user can continue to try various locations for the distal and proximal boundary indicators (FIG. 17), to make various measurements so as to be able to judge the best location to put the stent, what length the stent should be, and what diameter the stent should be. In this way, the OCT representation of the vessel and the lumen are configured as a deformable or modifiable representation that allows testing different stent placement scenarios.

As a result, the user can determine if more than one stent is required; whether the stent will block too many branch vessels; and whether the position of the ends of the stent ("the landing zones") will result in their being placed in an area of stenosis. The system also labels 297, 297' the diameters of the vessel at each of the boundary indicators 282, 282'. The two numbers present are current vessel lumen diameter (smaller number) and target lumen diameter (greater number). The system also provides a label 300 for a given point in the lumen 302 that lists the current lumen diameter (smaller number) and target lumen diameter (greater number) (generally 303), the MLA 304 and the percent area stenosis (AS) 305 which is given by the equation:

$$AS = (\text{Optimal Area} - \text{Current Area})/\text{Optimal Area} \qquad \text{Eqn. 6}$$

The system can also determine the target stent diameters of the stent ends. The target stent profile is calculated using the diameters of the vessel lumen. To do this, the algorithm makes several assumptions. First, the diameter of a lumen segment, which is the lumen between branches, is constant. As the lumen crosses the branches, the diameter of the lumen decreases so that the proximal diameter of the lumen is greater than the distal diameter. This incremental decrease in lumen diameter between lumen segments is proportional to the branch diameter between the lumen segments. Finally, the software-based implementation of the formula and diameter calculations and other steps described herein, includes an alert that warn the user that the ends of the stent are being placed in an area of lipid or calcium stenosis that can be ruptured.

As a result, the diameter of the target stent profile in a segment with the distal or proximal stent boundary is substantially equal to the actual of the lumen at that distal or proximal boundary. Further, the difference in the area between the proximal and distal boundaries is distributed among the segments between the two boundaries in proportion to the branch diameters between the segments. This means that the decrease in area between two segments is proportional to the diameter of the branch between the two segments.

If there are N branches, tone method or algorithm to determine the incremental change in the area $\delta_n$ of the stent at each branch (n) having branch area ($\text{branch}A_n$) is:

$$\Delta = \text{Proximal End Area} - \text{Distal End Area} \qquad \text{Eqn 7}$$

where $\Delta$ is the difference in the areas. This is equal to the sum of the incremental changes in area at each branch, summed over all (N) branches.

$$\Delta = \Sigma_{\text{from } n \text{ to } N} \delta_n \qquad \text{Eqn 8}$$

$$\delta_n \text{ is proportional to } \text{branch}A_n \qquad \text{Eqn 9}$$

$$\delta_n = (\text{branch}A_n * \Delta)/\Sigma_{\text{from } n \text{ to } N} \text{branch}A_n \qquad \text{Eqn 10}$$

Thus, the diameter change at each branch is:

$$d_n = \sqrt{(4\,\delta_n/\pi)} \qquad \text{Eqn 11}$$

There are some special cases worth considering. For example, if the stent is small enough to be placed within one segment, the stent profile is a straight line connecting the two ends and the two ends are of the same diameter. If the diameter of the lumen of the proximal cursor is less than the diameter of the distal cursor, then stent profile is a straight line connecting the two ends, but the two ends have different diameters.

Figure 18:
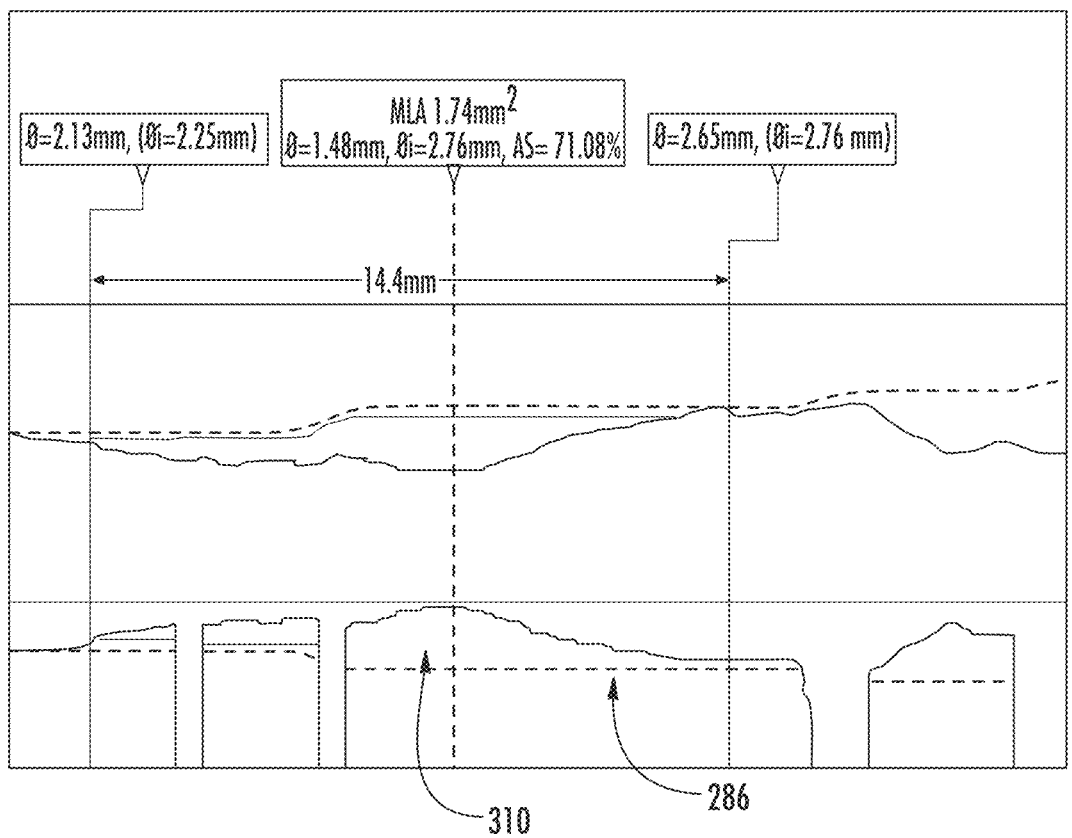
FIG. 18 is a screen shot of a portion of the graphic interface showing the difference between the target stent profile and target vessel profile.

Referring to FIG. 18, shown is a portion of the graphic interface depicting the difference between the target stent profile 310 and target lumen diameter profile 286. In use, the data from an OCT scan of the lumen is collected or retrieved from a database and the target lumen profile is produced by the system, methods, or components otherwise described. The system then calculates the target stent diameter using one or more algorithm and methods described herein. Alternatively, the system can try different stent placements based on user selected locations in the stent in the user interface.

The preceding description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic device, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is generally defined as a self-consistent sequence of operations leading to a desired result. The operations performed as method steps or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as is apparent from the following discussion, it is appreciated that throughout the description, discussions utilizing terms such as "processing" or "computing" or "displaying" or "calculating" or "comparing, "calibrating" "generating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention, in some embodiments, also relates to an apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, generating and propagating contours, filtering data, displaying regions, area and volume measurements, performing a medical device-specific action based on or in response to a parameter, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment, a module refers to a software routine, program, or other memory resident application suitable for receiving, transforming, routing and processing instructions, or various types of data such as measured probe parameters, quantitative parameters, encoding schemes, decoding schemes, calibration data, probe lengths, probe measurements, probe intensity, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

What is claimed is:

1. A method for sizing a stent for placement in a lumen of an artery comprising:
    receiving, by one or more processors from an intravascular device within the lumen of the artery, intravascular data including one or more image frames;
    generating, by the one or more processors based on the intravascular data, a representation of the artery, the representation composed of at least one of the one or more image frames;
    providing for output, by the one or more processors, the representation of the artery;
    dividing, by the one or more processors, the representation of the artery into a plurality of segments, each segment defined as a space between branches of the artery, wherein the representation of the artery being divided into N+1 inter-branch segments, wherein N is a number of branches of the representation of the artery;
    selecting, by the one or more processors, a first segment from the plurality of segments and defining a maximum diameter of the first segment;
    determining, by the one or more processors, a maximum diameter of a second segment based upon the defined maximum diameter of the first segment;
    determining, by the one or more processors based on the maximum diameter of the second segment, a maximum diameter of another segment of the plurality of segments;

iteratively proceeding, by the one or more processors, until a maximum diameter of each segment in the plurality of segments is determined;

automatically determining, by the one or more processors based on the determined maximum diameters, one or more landing zones corresponding to candidate positions for an end of the stent;

selecting, by the one or more processors based on the determined one or more landing zones, the stent for intravascular placement in the artery, wherein the selected stent is sized for placement in the lumen of the artery to increase blood flow therein;

providing for output, by the one or more processors, a representation of the selected stent on the previously provided representation of the artery.

2. The method of claim 1 wherein the maximum diameter of one of the plurality of segments is determined in response to a measured diameter of the segment, a calculated diameter of the segment and a quality value of the segment.

3. The method of claim 1, wherein when determining the maximum diameter of a given segment, the method further comprises determining, by the one or more processors, the maximum diameter of the given segment according to a power law, is further determined, wherein the power law is:

$$D^\varepsilon(i+1) = D^\varepsilon(i) + D_b^\varepsilon(i)$$

wherein D is the diameter of the given segment, $D_b$ is a diameter of a branch and ε is an exponent.

4. The method of claim 3 wherein ε has a value between 2.0 and 3.0, each segment being defined as the space between branches of the artery.

5. The method of claim 1, further comprising determining, by the one or more processors, a normalcy of tissue by a method selected from the group consisting of automated tissue characterization, user identification and morphology.

6. The method of claim 5 wherein the method of automated tissue characterization includes cross-correlating an optical coherence tomography signal between adjacent regions of the artery.

7. The method of claim 5 wherein the method of automated tissue characterization uses intima-media (IM) to outer adventitia (OA) ratios.

8. The method of claim 7 wherein representations of the segments are first filtered with a Gabor filter.

9. The method of claim 5 wherein the method of automated tissue characterization uses image frame based intensity profiles.

10. The method of claim 1 further comprising determining a stent contact location in the artery by determining an amount of disease present in the artery.

11. The method of claim 1, further comprising:
measuring, by the one or more processors, an actual diameter of the second segment; and
selecting, by the one or more processors, the greater one of the determined maximum diameter and the measured actual diameter as the maximum diameter.

12. An apparatus for sizing a stent for placement in an artery, the apparatus comprising:
one or more processors, the one or more processors configured to:
receive, from an intravascular imaging probe, intravascular data including one or more image frames;
generate, based on the intravascular data, a representation of the artery, the representation composed of at least one of the one or more image frames;
provide for output the representation of the artery;
divide the representation of the artery into a plurality of segments, each segment defined as a space between branches of the artery the representation of the artery being divided into N+1 inter-branch segments, where N is a number of branches of the representation of the artery;
select a first segment from the plurality of segments and defining a maximum diameter of the first segment;
determine, based upon the defined maximum diameter of the first segment, a maximum diameter of a segment adjacent to the first segment;
determine an actual diameter of the adjacent segment;
select the larger of the determined maximum diameter or the actual diameter as the selected maximum diameter of the adjacent segment;
use the selected maximum diameter to find a maximum diameter of another segment;
iteratively proceed until a maximum diameter of each segment in the plurality of segments is determined;
automatically determine, based on the determined maximum diameters, one or more landing zones for most effective stent placement to reduce the complexities of stent planning;
provide for output results of examining the plurality of segments to allow a user to select the stent for intravascular placement in a lumen of the artery in response to a detected maximum lumen diameter of an end proximal segment and a detected maximum lumen diameter of an end distal end segment; and
in response to receiving a selection of the stent, provide for output a representation of the selected stent on the previously provided representation of the artery.

13. The apparatus of claim 12 wherein the one or more processors determines the maximum diameter of one of the plurality of segments in response to a measured diameter of the segment, a calculated diameter of the segment and a quality value of the segment.

14. The apparatus of claim 12 wherein the one or more processors determines the diameter of a segment according to a power law given:

$$D^\varepsilon(i+1) = D^\varepsilon(i) + D_b^\varepsilon(i)$$

wherein D is the diameter of the segment, $D_b$ is diameter of a branch and ε is an exponent.

15. The apparatus of claim 14 wherein ε has a value between 2.0 and 3.0.

16. The apparatus of claim 12, wherein the one or more processors are further configured to determine a normalcy of tissue by a method selected from the group consisting of automated tissue characterization, user identification and morphology.

17. The apparatus of claim 16, wherein automated tissue characterization utilizes cross-correlation of optical coherence tomography (OCT) signal between adjacent regions of the artery.

18. The apparatus of claim 16 wherein automated tissue characterization uses IM to OA ratios.

19. The apparatus of claim 18 wherein the one or more processors first filters image data of the artery segments using a Gabor filter.

20. The apparatus of claim 12 wherein displaying results of examining the plurality of segments further comprises displaying a representation of the artery configured to provide feedback to a user in response to different stent placement scenarios.

21. The apparatus of claim 12 wherein one or more programs further comprise determining a stent contact location in the artery by determining an amount of disease present in the artery.

* * * * *

UNITED STATES PATENT AND TRADEMARK OFFICE
CERTIFICATE OF CORRECTION

PATENT NO. : 11,923,067 B2
APPLICATION NO. : 14/115527
DATED : March 5, 2024
INVENTOR(S) : Joseph M. Schmitt et al.

Page 1 of 1

It is certified that error appears in the above-identified patent and that said Letters Patent is hereby corrected as shown below:

In the Claims

Column 19, Line 12, after "blood flow therein;" add -- and --.
Column 19, Line 29, after "wherein D is" delete "the" and add -- a --.
Column 19, Line 56, after "more processors," delete "the" and add -- a --.
Column 20, Line 61, after "data of the" delete "artery" and add -- plurality of --.

Signed and Sealed this
Seventeenth Day of September, 2024

Katherine Kelly Vidal
*Director of the United States Patent and Trademark Office*